(12) United States Patent
Borsody

(10) Patent No.: US 10,105,549 B2
(45) Date of Patent: Oct. 23, 2018

(54) MODULATING FUNCTION OF NEURAL STRUCTURES NEAR THE EAR

(71) Applicant: Nervive, Inc., Orinda, CA (US)

(72) Inventor: Mark Klingler Borsody, Orinda, CA (US)

(73) Assignee: Nervive, Inc., Orinda, CA (US)

( * ) Notice: Subject to any disclaimer, the term of this patent is extended or adjusted under 35 U.S.C. 154(b) by 260 days.

(21) Appl. No.: 15/056,326

(22) Filed: Feb. 29, 2016

(65) Prior Publication Data
US 2016/0175605 A1    Jun. 23, 2016

Related U.S. Application Data

(63) Continuation of application No. 13/692,226, filed on Dec. 3, 2012, now Pat. No. 9,272,157, which is a
(Continued)

(51) Int. Cl.
*A61N 2/00* (2006.01)
*A61N 2/02* (2006.01)
(Continued)

(52) U.S. Cl.
CPC ............. *A61N 2/006* (2013.01); *A61N 2/02* (2013.01); *A61N 1/40* (2013.01); *A61N 5/0622* (2013.01); *A61N 2007/0026* (2013.01)

(58) Field of Classification Search
CPC ........ A61N 2/006; A61N 2/02; A61N 5/0622; A61N 2007/0026; A61N 1/40
See application file for complete search history.

(56) References Cited

U.S. PATENT DOCUMENTS

| 2,876,767 A | 3/1959 | Wasserman |
|---|---|---|
| 3,629,521 A | 12/1971 | Puharich et al. |

(Continued)

FOREIGN PATENT DOCUMENTS

| CA | 1 135 348 A | 11/1982 |
|---|---|---|
| CA | 2 021 506 A1 | 2/1991 |

(Continued)

OTHER PUBLICATIONS

Australian Government, IP Australia, Patent Examination Report No. 1, Australian Patent Application No. 2011248487, Feb. 17, 2015, three pages.
(Continued)

*Primary Examiner* — Christine H Matthews
*Assistant Examiner* — Joshua D Lannu
(74) *Attorney, Agent, or Firm* — Fenwick & West LLP

(57) ABSTRACT

Stimulation of the facial nerve system (e.g., electrically, electromagnetically, etc.) in ischemic stroke patients will cause dilation of occluded arteries and dilation of surrounding arteries, allowing for blood flow to circumvent the obstruction and reach previously-deprived tissue. The device approaches the facial nerve and its branches in the vicinity of the ear. In use, the device can be inserted into the ear canal and/or placed in proximity to the ear in order to stimulate the facial nerve system non-invasively (e.g., using an electromagnetic field). The device can be used in the emergency treatment of acute stroke or chronically variations for long-term maintenance of blood flow to the brain and stroke prevention. Additional embodiments of the device may be adapted for use on different regions of the body.

19 Claims, 18 Drawing Sheets

Related U.S. Application Data continuation-in-part of application No. 13/096,889, filed on Apr. 28, 2011, now Pat. No. 9,339,645.

(60) Provisional application No. 61/676,631, filed on Jul. 27, 2012, provisional application No. 61/624,958, filed on Apr. 16, 2012, provisional application No. 61/633,371, filed on Feb. 10, 2012, provisional application No. 61/630,150, filed on Dec. 6, 2011, provisional application No. 61/397,462, filed on Jun. 14, 2010, provisional application No. 61/330,366, filed on May 2, 2010.

(51) Int. Cl.
  *A61N 5/06* (2006.01)
  *A61N 7/00* (2006.01)
  *A61N 1/40* (2006.01)

(56) References Cited

U.S. PATENT DOCUMENTS

| | | |
|---|---|---|
| 4,044,774 A | 8/1977 | Corbin et al. |
| 4,696,287 A | 9/1987 | Hortmann et al. |
| 5,116,304 A | 5/1992 | Cadwell |
| 5,441,495 A | 8/1995 | Liboff et al. |
| 5,461,215 A | 10/1995 | Haldeman |
| 5,607,461 A | 3/1997 | Lathrop |
| 5,922,016 A | 7/1999 | Wagner |
| 5,991,664 A | 11/1999 | Seligman |
| 6,078,838 A | 6/2000 | Rubinstein |
| 6,093,417 A | 7/2000 | Petrus |
| 6,179,770 B1 | 1/2001 | Mould |
| 6,179,771 B1 | 1/2001 | Mueller |
| 6,179,772 B1 | 1/2001 | Blackwell |
| 6,213,933 B1 | 4/2001 | Lin |
| 6,310,961 B1 | 10/2001 | Oliveira et al. |
| 6,408,855 B1 | 6/2002 | Berrang et al. |
| 6,425,852 B1 | 7/2002 | Epstein et al. |
| 6,468,199 B1 | 10/2002 | Satou et al. |
| 6,488,617 B1 | 12/2002 | Katz |
| 6,526,318 B1 | 2/2003 | Ansarinia |
| 6,541,966 B1 | 4/2003 | Keene |
| 6,551,233 B2 | 4/2003 | Perreault et al. |
| 6,629,399 B2 | 10/2003 | Sarles et al. |
| 6,663,556 B2 | 12/2003 | Barker |
| 6,849,040 B2 | 2/2005 | Ruohonen et al. |
| 6,853,858 B2 | 2/2005 | Shalev |
| 6,900,420 B2 | 5/2005 | Markegård et al. |
| 6,926,660 B2 | 8/2005 | Miller |
| 7,103,417 B1 | 9/2006 | Segel et al. |
| 7,117,033 B2 | 10/2006 | Shalev et al. |
| 7,120,489 B2 | 10/2006 | Shalev et al. |
| 7,146,209 B2 | 12/2006 | Gross et al. |
| 7,146,227 B2 | 12/2006 | Dadd et al. |
| 7,149,574 B2 | 12/2006 | Yun et al. |
| 7,340,298 B1 | 3/2008 | Barbut |
| 7,363,076 B2 | 4/2008 | Yun et al. |
| 7,367,936 B2 | 5/2008 | Myers et al. |
| 7,396,326 B2 | 7/2008 | Ghiron et al. |
| 7,407,478 B2 | 8/2008 | Zangen et al. |
| 7,519,435 B2 | 4/2009 | Parker et al. |
| 7,561,919 B2 | 7/2009 | Shalev et al. |
| 7,580,754 B2 | 8/2009 | Zhang et al. |
| 7,591,776 B2 | 9/2009 | Phillips et al. |
| 7,591,779 B2 | 9/2009 | Kalinowski et al. |
| 7,601,115 B2 | 10/2009 | Riehl |
| 7,636,597 B2 | 12/2009 | Gross et al. |
| 7,640,062 B2 | 12/2009 | Shalev |
| 7,658,704 B2 | 2/2010 | Fox et al. |
| 7,684,858 B2 | 3/2010 | He et al. |
| 7,684,859 B2 | 3/2010 | Shalev et al. |
| 7,711,432 B2 | 5/2010 | Thimineur et al. |
| 7,771,341 B2 | 8/2010 | Rogers |
| 7,854,232 B2 | 12/2010 | Aho et al. |
| 7,946,973 B2 | 5/2011 | Peterchev |
| 7,973,635 B2 | 7/2011 | Baarman et al. |
| 7,976,451 B2 | 7/2011 | Zangen et al. |
| 7,998,053 B2 | 8/2011 | Aho |
| 8,052,591 B2 | 11/2011 | Mishelevich et al. |
| 8,267,850 B2 | 9/2012 | Schneider et al. |
| 8,277,371 B2 | 10/2012 | Zangen et al. |
| 8,388,510 B2 | 3/2013 | Zangen et al. |
| 8,396,566 B2 | 3/2013 | Kassab et al. |
| 8,412,342 B2 | 4/2013 | Zhang et al. |
| 8,460,167 B2 | 6/2013 | Chornenky et al. |
| 8,523,753 B2 | 9/2013 | Schneider et al. |
| 8,545,378 B2 | 10/2013 | Peterchev |
| 8,591,392 B2 | 11/2013 | Bentwich et al. |
| 8,723,628 B2 | 5/2014 | Mishelevich et al. |
| 8,771,163 B2 | 7/2014 | Zangen et al. |
| 8,795,148 B2 | 8/2014 | Schneider et al. |
| 2001/0031906 A1 | 10/2001 | Ishikawa et al. |
| 2002/0026125 A1 | 2/2002 | Leysieffer |
| 2002/0151886 A1 | 10/2002 | Wood |
| 2003/0004393 A1 | 1/2003 | Ewing et al. |
| 2003/0195588 A1 | 10/2003 | Fischell et al. |
| 2004/0220644 A1 | 11/2004 | Shalev |
| 2005/0027251 A1 | 2/2005 | Masters |
| 2005/0222486 A1 | 10/2005 | Shin et al. |
| 2005/0288664 A1 | 12/2005 | Ford et al. |
| 2006/0122675 A1 | 6/2006 | Libbus et al. |
| 2006/0162952 A1 | 7/2006 | Olbrich et al. |
| 2006/0187607 A1 | 8/2006 | Mo |
| 2006/0287566 A1 | 12/2006 | Zangen et al. |
| 2006/0287689 A1 | 12/2006 | Debruyne et al. |
| 2007/0118197 A1 | 5/2007 | Loeb |
| 2008/0027513 A1 | 1/2008 | Carbunaru |
| 2008/0058581 A1 | 3/2008 | Aho |
| 2008/0082141 A1 | 4/2008 | Risi |
| 2008/0097549 A1 | 4/2008 | Colbaugh et al. |
| 2008/0154343 A1 | 6/2008 | Li et al. |
| 2008/0224808 A1 | 9/2008 | Ghiron et al. |
| 2008/0262287 A1 | 10/2008 | Dussau |
| 2008/0262468 A1 | 10/2008 | Clifford et al. |
| 2009/0018384 A1 | 1/2009 | Boyden et al. |
| 2009/0099405 A1 | 4/2009 | Schneider et al. |
| 2009/0108969 A1 | 4/2009 | Sims et al. |
| 2009/0131739 A1 | 5/2009 | Shalev |
| 2009/0174407 A1 | 7/2009 | Han et al. |
| 2009/0187098 A1 | 7/2009 | Makower et al. |
| 2010/0003656 A1* | 1/2010 | Kilgard ............ A61N 1/36014 434/262 |
| 2010/0016650 A1 | 1/2010 | Phillips et al. |
| 2010/0094076 A1 | 4/2010 | Phillips |
| 2010/0113959 A1 | 5/2010 | Pascual-Leone et al. |
| 2010/0114184 A1 | 5/2010 | Degtyar et al. |
| 2010/0193506 A1 | 8/2010 | Nagai et al. |
| 2010/0286470 A1 | 11/2010 | Schneider et al. |
| 2010/0331602 A1 | 12/2010 | Mishelevich et al. |
| 2011/0082326 A1 | 4/2011 | Mishelevich et al. |
| 2011/0125203 A1 | 5/2011 | Simon et al. |
| 2011/0218381 A1 | 9/2011 | Ruohonen |
| 2011/0263925 A1 | 10/2011 | Bratton |
| 2011/0270361 A1 | 11/2011 | Borsody |
| 2011/0306846 A1 | 12/2011 | Osorio |
| 2012/0101366 A1 | 4/2012 | Ruohonen et al. |
| 2012/0149969 A1 | 6/2012 | Farone |
| 2013/0096363 A1 | 4/2013 | Schneider et al. |
| 2013/0267763 A1 | 10/2013 | Schneider et al. |
| 2013/0278369 A1 | 10/2013 | Shepard et al. |
| 2013/0282071 A1 | 10/2013 | Matos |
| 2013/0304159 A1 | 11/2013 | Simon et al. |
| 2013/0317281 A1 | 11/2013 | Schneider et al. |
| 2014/0081072 A1 | 3/2014 | Huang et al. |
| 2014/0085031 A1 | 3/2014 | Nomura et al. |
| 2014/0163305 A1 | 6/2014 | Watterson |

FOREIGN PATENT DOCUMENTS

| | | |
|---|---|---|
| CA | 2 608 084 A1 | 11/2006 |
| CA | 2 610 991 A1 | 12/2006 |
| CN | 86105171 A | 3/1987 |
| CN | 101366666 A | 2/2009 |

(56) References Cited

FOREIGN PATENT DOCUMENTS

| | | |
|---|---|---|
| CN | 101985058 A | 3/2011 |
| CN | 102013579 A | 4/2011 |
| CN | 202605538 U | 12/2012 |
| CN | 202637725 U | 1/2013 |
| CN | 202961526 U | 6/2013 |
| DE | 10046275 A1 | 3/2002 |
| EP | 0 214 527 A1 | 3/1987 |
| EP | 0 408 230 A2 | 1/1991 |
| EP | 1 145 738 B1 | 10/2001 |
| EP | 1 671 672 A1 | 6/2006 |
| EP | 1 890 762 A2 | 2/2008 |
| EP | 1 890 615 A4 | 9/2009 |
| EP | 2 384 223 A2 | 11/2011 |
| EP | 2 520 334 A1 | 11/2012 |
| EP | 2 666 515 A1 | 11/2013 |
| GB | 2261820 | 6/1993 |
| JP | S62-44250 A | 2/1987 |
| JP | 2003-503119 A | 1/2003 |
| JP | 2003-180847 A | 7/2003 |
| JP | 2006-515999 A | 6/2006 |
| JP | 2008-522725 A | 7/2008 |
| JP | 2008-528145 A | 7/2008 |
| JP | 2010-213979 A | 9/2010 |
| RU | 2012 115 948 A | 10/2013 |
| WO | WO 1995/25417 A1 | 9/1995 |
| WO | WO 1997/00639 A2 | 1/1997 |
| WO | WO 2001/00273 A1 | 1/2001 |
| WO | WO 2001/97095 A2 | 12/2001 |
| WO | WO 2001/97905 A1 | 12/2001 |
| WO | WO 2002/32504 A2 | 4/2002 |
| WO | WO 2002/089902 A2 | 11/2002 |
| WO | WO 2003/026478 A2 | 4/2003 |
| WO | WO 2003/090863 A1 | 11/2003 |
| WO | WO 2004/036603 A1 | 4/2004 |
| WO | WO 2004/043217 A2 | 5/2004 |
| WO | WO 2004/043218 A2 | 5/2004 |
| WO | WO 2004/043334 A2 | 5/2004 |
| WO | WO 2004/045242 A2 | 5/2004 |
| WO | WO 2004/087255 A1 | 10/2004 |
| WO | WO 2005/002346 A2 | 1/2005 |
| WO | WO 2005/030025 A2 | 4/2005 |
| WO | WO 2006/014896 A1 | 2/2006 |
| WO | WO 2006/021957 A2 | 3/2006 |
| WO | WO 2006/040690 A2 | 4/2006 |
| WO | WO 2006/057734 A1 | 6/2006 |
| WO | WO 2006/076708 A2 | 7/2006 |
| WO | WO 2006/078924 A2 | 7/2006 |
| WO | WO 2006/083675 A2 | 8/2006 |
| WO | WO 2006/119512 A2 | 11/2006 |
| WO | WO 2006/134598 A3 | 12/2006 |
| WO | WO 2006/135853 A2 | 12/2006 |
| WO | WO 2007/137335 A1 | 12/2007 |
| WO | WO 2008/030485 A2 | 3/2008 |
| WO | WO 2008/048471 A2 | 4/2008 |
| WO | WO 2008/052166 A2 | 5/2008 |
| WO | WO 2008/112915 A1 | 9/2008 |
| WO | WO 2008/130533 A2 | 10/2008 |
| WO | WO 2008/150963 A1 | 12/2008 |
| WO | WO 2009/011939 A1 | 1/2009 |
| WO | WO 2009/013881 A1 | 1/2009 |
| WO | WO 2009/033144 A2 | 3/2009 |
| WO | WO 2009/033150 A1 | 3/2009 |
| WO | WO 2009/033192 A1 | 3/2009 |
| WO | WO 2009/037689 A2 | 3/2009 |
| WO | WO 2009/042863 A1 | 4/2009 |
| WO | WO 2009/047370 A2 | 4/2009 |
| WO | WO 2009/100633 A1 | 8/2009 |
| WO | WO 2009/138428 A2 | 11/2009 |
| WO | WO 2009/143171 A2 | 11/2009 |
| WO | WO 2010/014894 A1 | 2/2010 |
| WO | WO 2010/033909 A2 | 3/2010 |
| WO | WO 2010/049576 A1 | 5/2010 |
| WO | WO 2010/062622 A2 | 6/2010 |
| WO | WO 2010/080879 A2 | 7/2010 |
| WO | WO 2011/060699 A1 | 5/2011 |
| WO | WO 2012/045079 A9 | 4/2012 |
| WO | WO 2012/048319 A2 | 4/2012 |
| WO | WO 2012/090068 A2 | 7/2012 |
| WO | WO 2012/117166 A1 | 9/2012 |
| WO | WO 2013/006670 A2 | 1/2013 |
| WO | WO 2013/116235 A1 | 8/2013 |
| WO | WO 2013/126176 A1 | 8/2013 |
| WO | WO 2014/022236 A1 | 2/2014 |
| WO | WO 2014/097571 A1 | 6/2014 |

OTHER PUBLICATIONS

Bar-Shir, A. et al., "Late Stimulation of the Sphenopalatine-Ganglion in Ischemic Rats: Improvement in N-Acetyl-Aspartate Levels and Diffusion Weighted Imaging Characteristcs as Seen by MR," Journal of Magnetic Resonance Imaging, 2010, pp. 1355-1363, vol. 31.

Brainsgate, "Ischemic Stroke System," 2005, two pages. [Online] [Retrieved Oct. 19, 2011] Retrieved from the Internet <URL:http://www.brainsgate.com/eng/page.php?id=11&instance.sub.--id=8&-gt;.

European Patent Office, Search Report and Opinion, European Patent Application No. 11778023.9, dated Jul. 31, 2014, eight pages.

European Patent Office, Search Report and Opinion, European Patent Application No. 12856454.9, dated Oct. 19, 2015, six pages.

Goadsby, P.J., "Characteristics of facial nerve-elicited cerebral vasodilatation determined using laser Doppler flowmetry," Database Accession No. NLM1992824, Jan. 1991, XP002711162, Database Medline, U.S. National Library of Medicine (NLM), Bethesda, Maryland, U.S.

Japanese Patent Office, Office Action, Japanese Patent Application No. 2013-509125, dated Oct. 1, 2014, eight pages.

Khurana, D. et al., "Implant for Augmentation of Cerebral Blood Flow Trial 1: A pilot Study Evaluating the Safety and Effectiveness of the Ischaemic Stroke System for Treatment of Acute Ischaemic Stroke," International Journal of Stroke, Dec. 2009, pp. 480-485, vol. 4.

PCT International Search Report and Written Opinion, PCT Application No. PCT/US2011/034378, dated Aug. 8, 2011, seven pages.

PCT International Search Report and Written Opinion, PCT Application No. PCT/US2012/067801, dated Apr. 19, 2013, twelve pages.

State Intellectual Property Office of the People's Republic of China, First Office Action, Chinese Patent Application No. 201180022239.3, dated Apr. 4, 2014, fifteen pages.

State Intellectual Property Office of the People's Republic of China, First Office Action, Chinese Patent Application No. 2012800598917, dated Mar. 19, 2015, sixteen pages.

Stjernschantz, J. et al., "Vasomotor effects of facial nerve stimulation: noncholinergic vasodilation in the eye," Acta Physiologica Scandinavica, May 1, 1980, pp. 45-50, vol. 109, No. 1, Scandinavian Physiological Society.

United States Office Action, U.S. Appl. No. 13/096,889, dated Jun. 18, 2014, twenty-five pages.

United States Office Action, U.S. Appl. No. 13/096,889, dated Jun. 26, 2015, thirteen pages.

United States Office Action, U.S. Appl. No. 13/096,889, dated Nov. 6, 2014, twenty-seven pages.

Yarnitsky, D. et al., "Blood-brain Barrier Opened by Stimulation of the Parasympathetic Sphenopalatine Ganglion: A New Method for Macromolecule Deliver to the Brain," Journal of Neurosurgery, 2004, pp. 303-309, vol. 101.

Yarnitsky, D. D et al., "Increased BBB Permeability by Parasympathetic Sphenopalatine Ganglion Stimulation in Dogs," Brain Research, 2004, five pages.

Yarnitsky, D. et al., "Reversal of Cerebral Vasospasm by Sphenopalatine Ganglion Stimulation in a Dog Model of Subarachnoid Hemorrahage," Surgical Neurology, 2005, pp. 5-11, vol. 64.

Israel Patent Office, Office Action, Israeli Patent Application No. 222750, dated May 3, 2015, six pages.

Office Action for U.S. Appl. No. 13/692,226, dated Sep. 9, 2014, 23 Pages.

(56) References Cited

OTHER PUBLICATIONS

Office Action for U.S. Appl. No. 13/692,226, dated Jun. 10, 2014, 19 Pages.
Office Action for U.S. Appl. No. 13/692,226, dated Apr. 9, 2015, 18 Pages.
Communication pursuant to Article 94(3) EPC for European Patent Application No. EP 12856454.9, dated Apr. 10, 2018, 9 Pages.
Office Action for Indian Patent Application No. 8945/CHENP/2012, dated May 29, 2018, 5 Pages.

* cited by examiner

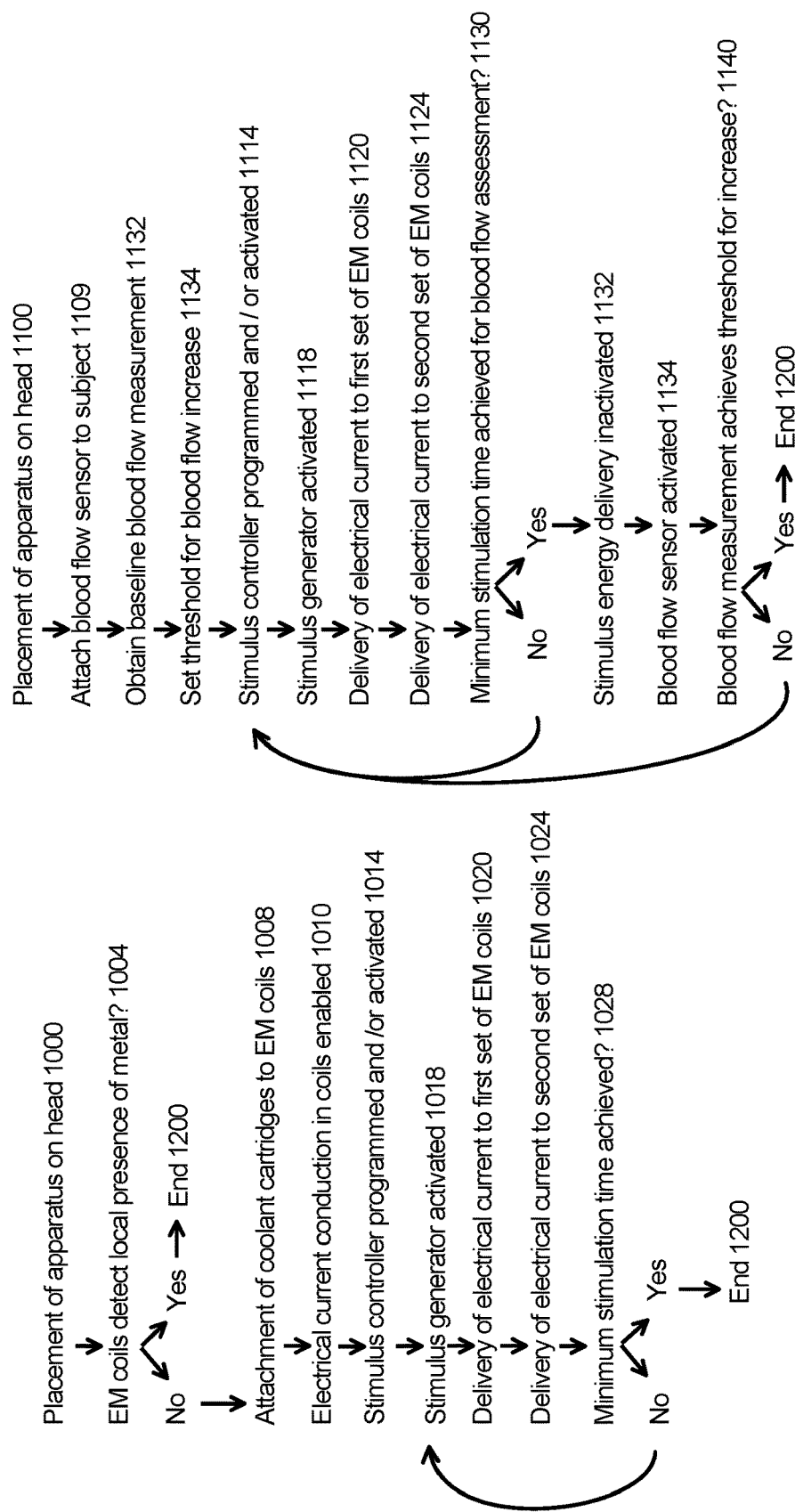

MODULATING FUNCTION OF NEURAL STRUCTURES NEAR THE EAR

CROSS REFERENCE TO RELATED APPLICATIONS

This application is a continuation of prior, co-pending U.S. application Ser. No. 13/692,226, filed Dec. 3, 2012, entitled "Modulating Function of Neural Structures Near the Ear," which claims the benefit of U.S. Provisional Application No. 61/676,631, filed on Jul. 27, 2012, entitled "Apparatus and means of use for modulating the function of neural structures within and near the middle ear," U.S. Provisional Application No. 61/624,958, filed on Apr. 16, 2012, entitled "Apparatus and means of use for modulating the function of neural structures within and near the middle ear," U.S. Provisional Application No. 61/633,371, filed on Feb. 10, 2012, entitled "Apparatus and means of use for modulating the function of neural structures within and near the middle ear," and U.S. Provisional Application No. 61/630,150, filed on Dec. 6, 2011, entitled "Apparatus and means of use for modulating the function of neural structures within and near the middle ear." U.S. application Ser. No. 13/692,226 is also a continuation-in-part U.S. application Ser. No. 13/096,889, filed Apr. 28, 2011, which claims the benefit of U.S. Provisional Application No. 61/397,462, filed on Jun. 14, 2010, entitled "Apparatus and Means of Use for Modulating the Function of Neural Structures within and near to the Middle Ear," and of U.S. Provisional Application No. 61/330,366, filed on May 2, 2010, entitled "Apparatus and Means of Use for Modulating the Function the Tympanic Plexus, Geniculate Ganglion, Facial Nerve and/or Related Neural Structures of the Middle Ear." Each of the above-referenced applications is hereby incorporated by reference herein in their entireties for all purposes.

BACKGROUND OF THE INVENTION

Field of the Invention

The invention relates to apparatuses and methods for treatment of conditions caused directly or indirectly by functions of the vasculature. More specifically, the invention relates to apparatuses and methods for treatment of conditions related to the cranial vasculature, and even more specifically to modulating the function of particular neural structures in the vicinity of the ear for treatment of stroke and other conditions.

Description of the Related Art

Stroke is the most common cause of physical disability and the third most common cause of death in the United States. Nearly 900,000 cases of stroke occur each year in the United States, costing $69 billion in healthcare costs. Worldwide, there are nearly 15 million cases of stroke annually; the cost of healthcare services and lost productivity on such a scale is incalculable.

Most cases of stroke are caused by loss of blood flow to the brain because of occlusion of a cerebral artery or carotid artery. Artery occlusion commonly results from (1) a blood clot that is carried by the blood flow into an artery in which it becomes lodged or (2) by formation of a blood clot upon an area of atherosclerotic plaque inside the artery. Loss of blood flow by either mechanism, or by any of several less-common mechanisms, deprives areas of the brain fed by the artery of nutrients and oxygen, leading to cell death and tissue necrosis.

The emergency treatment of stroke is limited. Only one drug, the thrombolytic tissue plasminogen activator (tPA; Alteplase), has been approved for the treatment of acute stroke in the United States. Alteplase acts to dissolve blood clots such as those that occlude cerebral and carotid arteries, causing stroke. As a result, Alteplase can also cause severe intracranial hemorrhage, which is its most serious complication. In order to reduce the chance of intracranial hemorrhage, Alteplase is subject to numerous restrictions that ultimately limit its use to only about 5% of all ischemic stroke patients.

In addition to Alteplase, endovascular techniques employing intra-arterial catheters are used to treat acute stroke. Endovascular techniques, based largely on retrieval of the blood clot from the cerebral or carotid artery or else local administration of thrombolytic drugs directly onto the blood clot, are costly and dangerous, and their use is limited to large hospitals that have highly-trained endovascular physicians on staff. Accordingly, only several thousand stroke patients are treated with endovascular techniques each year in the United States.

A possible treatment of stroke currently under development is electrical stimulation of the sphenopalatine ganglion. This potential treatment involves placement of a metal rod through the roof of the mouth (hard palate) into the vidian canal, which leads to the sphenopalatine ganglion. This device and method has a number of drawbacks. First, placement of the rod requires specialized training and equipment that will restrict its use to the largest and best-equipped hospitals. By inserting the rod through the mouth into the vidian canal, there is a risk of introducing dangerous oral bacteria into the bones of the face. In addition, the blind insertion of the rod into the confines of the vidian canal (which not only leads to the sphenopalatine ganglion but also contains the vidian artery and nerve) risks inducing bleeding or nerve injury. Stroke patients also commonly have difficulty swallowing as part of their neurological injury. Procedures implanting foreign bodies in the mouth, as required by this method, may lead to aspiration in patients who have airways already compromised by the neurological injury from stroke. Finally, this device and method only stimulates the sphenopalatine ganglion and its immediate connections, which in animals has a small effect on blood flow to the brain compared to stimulation of the nerve trunk. Furthermore, this device under development is only applied to one of the two sphenopalatine ganglia, neglecting the potentially additive effect of stimulating both ganglia.

Because of the magnitude of the disease and the limited treatments for it, a significant unmet medical need exists in acute stroke. Thus, there is a need for a solution that solves the problems with current acute stroke treatments noted above, and that: (a) does not require highly-trained endovascular physicians or specialized training for use; (b) does not risk intracranial hemorrhage, aspiration injury, bleeding and nerve injury, or facial bone infection; and (c) is non- or minimally-invasive.

SUMMARY OF THE INVENTION

Disclosed herein is a medical device and method-of-use that solves the above problems and that improves blood flow to the brain by causing dilation of the cerebral and carotid arteries using the body's own regulation of that vascular bed. The invention is an apparatus and method for modulating function of neural structures for treatment of stroke and other conditions. In one embodiment, the apparatus is a stimulator that causes dilation (relaxation) of the cerebral arteries. The cerebral and carotid arteries are innervated by nerves originating in the brainstem ("cranial nerves"), one of which—the facial nerve (also known as the 7$^{th}$ cranial nerve)—acts or else contains or is associated with components that act to regulate those arteries. Stimulation of the facial nerve system in ischemic stroke patients may then cause dilation of the arteries supplying the brain and the head, allowing for blood flow to circumvent an obstruction and reach previously deprived brain tissue. However, stimulation of the facial nerve in hemorrhagic stroke patients may fail to dilate the arteries of the brain and/or head, or else cause constriction of the arteries supplying the brain and/or head, beneficially reducing the likelihood of additional hemorrhage from the site of arterial rupture. The apparatus and method may be used to modify the function of numerous additional neural structures, including the entry region of the facial nerve into the internal auditory canal/internal acoustic meatus, the geniculate ganglion, the tympanic plexus, paratympanic organ(s), the intermediate nerve (of Wrisberg), the pterygopalatine/sphenopalatine nerves and ganglion, the petrosal nerves, the ethmoidal nerves, the palatine nerves, the vidian nerve, the sensory and motor fibers of any of the aforementioned structures, fibers of passage through the aforementioned structures, the communicating branches and connections of the aforementioned structures, and the communicating branches and connections between the aforementioned structures and the ophthalmic, trigeminal, glossopharyngeal, cervical, or vagal nerves.

We have discovered in preclinical/animal studies of subarachnoid hemorrhage and intracerebral hemorrhage that hematomas from these hemorrhages, once stable in size, do not enlarge after stimulation of the facial nerve using stimulation parameters that are otherwise effective at increasing cerebral blood flow in ischemic stroke. In ischemic stroke, we have demonstrated that facial nerve stimulation improves blood flow to the brain and also increases blood flow to the tissues of the head outside of the skull. In contrast, in hemorrhagic stroke, stimulation of the facial nerve does not appear to significantly increase blood flow to the brain, and it dramatically reduces blood flow to the tissues of the head outside of the skull. Thus, most of the embodiments of the device we describe herein are intended to be applied to a stroke patient without knowing if the patient has an ischemic or hemorrhagic stroke.

This property of the facial nerve, i.e., to withhold dilating cranial arteries and increasing cranial blood flow in the condition of hemorrhagic stroke, may reflect sensitivity to blood products, elevated intracranial pressure, or other properties of the hemorrhagic stroke. This property of the facial nerve may in part be mediated by additional neural structures including but not limited to sensory branches of the ophthalmic, trigeminal, glossopharyngeal, cervical, and vagus nerves, or by the circumventricular organs of the brain.

Thus, the invention may have different effects depending on the type of stroke a patient is experiencing. Furthermore, in some methods of use, the invention may serve to diagnose, or support the diagnosis, of stroke subtype (i.e., ischemic stroke versus hemorrhagic stroke) by virtue of the different blood flow responses induced by facial nerve stimulation in the different subtypes of stroke.

In one embodiment, the apparatus approaches the facial nerve and its branches as they pass through and near to the ear in a non-invasive manner. The apparatus can be used in the emergency treatment of acute stroke or can be employed for chronic use in the long-term maintenance of blood flow to the brain, e.g., in people with atherosclerotic disease of the cerebral vasculature in whom blood flow to parts of the brain is chronically compromised, or in patients with certain kinds of dementia. In comparison to the above-described sphenopalatine ganglion stimulator device under development that is inserted into the roof of the mouth, the invention described herein may stimulate the entire facial nerve, which activates the sphenopalatine ganglion as well as several other nerves, nerve branches, and ganglia, and which has a larger and/or more widespread effect on blood flow to the brain.

The apparatus is generally comprised of one or more electrically-conductive elements, such as one or more electrodes or electrically-conductive wires that, when provided electrical current, generates stimulation energy, such as energy in the form of one or more electromagnetic (EM) fields. The stimulation energy might also take the form of heat, ultrasound, radio frequency, microwave, infrared, ultraviolet, and electrical energy. In an embodiment where the stimulation energy takes the electromagnetic (EM) form, the EM field(s) are formed, shaped, distorted, or otherwise generated in a manner to activate the facial nerve system. In some embodiments, the electrically-conductive element is shaped substantially as a coil. In some embodiments, electrically-conductive elements are placed on both sides of the head and/or neck. In some embodiments, the electrically-conductive element is positioned on the head in such a manner as to orient the focus of the EM field or to summate multiple EM fields on a part of the facial nerve. In some embodiments, the orientation of the element is based on one or more anatomical structures of the head or neck. The apparatus can also include an energy regulating housing that can contain or house at least a part of the electrically-conductive element(s). Where there is more than one electrically conductive element, there may be separate housings for each element or a single housing for all elements. The housing electrically insulates the electrically-conductive element and/or dissipates heat in a desirable manner.

The apparatus also comprises a stimulus generator in electrical communication/direct connection with the electrically-conductive element(s) for supplying stimulus energy to the electrically-conductive element(s) for stimulating a neural system, such as one or more components of the facial nerve system in the vicinity of the ear. In some embodiments where the electrically-conductive element takes the form of an array of electrically conductive wires the stimulus generator is attached to these arrays that deliver stimulus energy, whereas in other embodiments the stimulus generator also serves as the arrays of electrically-conductive wire. The apparatus also includes a power source in electrical communication with the stimulus generator for providing power to the stimulus generator to supply the electrical current to the electrically-conductive element (e.g., arrays of electrically-conductive wire). In some embodiments, the stimulus generator is regulated, programmed, or directed by a stimulus controller. In some embodiments, the stimulus controller is guided, directed, programmed, or informed by a variety of sensors. As used herein, the term "stimulator" refers to the overall apparatus and its components.

BRIEF DESCRIPTION OF THE DRAWINGS

These and other features, aspects, and advantages of the present invention will become better understood with regard to the following description and accompanying drawings where:

FIG. 14 depicts a method-of-use for an apparatus in which activation of the apparatus requires a local metal detection function and attachment of coolant cartridges as safety measures, and in which activation of a stimulus generator is directed by a stimulus controller.

FIG. 15 depicts a method-of-use for an apparatus in which the ongoing delivery of electrical energy from a stimulus generator to the EM coils is limited by a blood flow sensor and a timer.

Figure 1A:
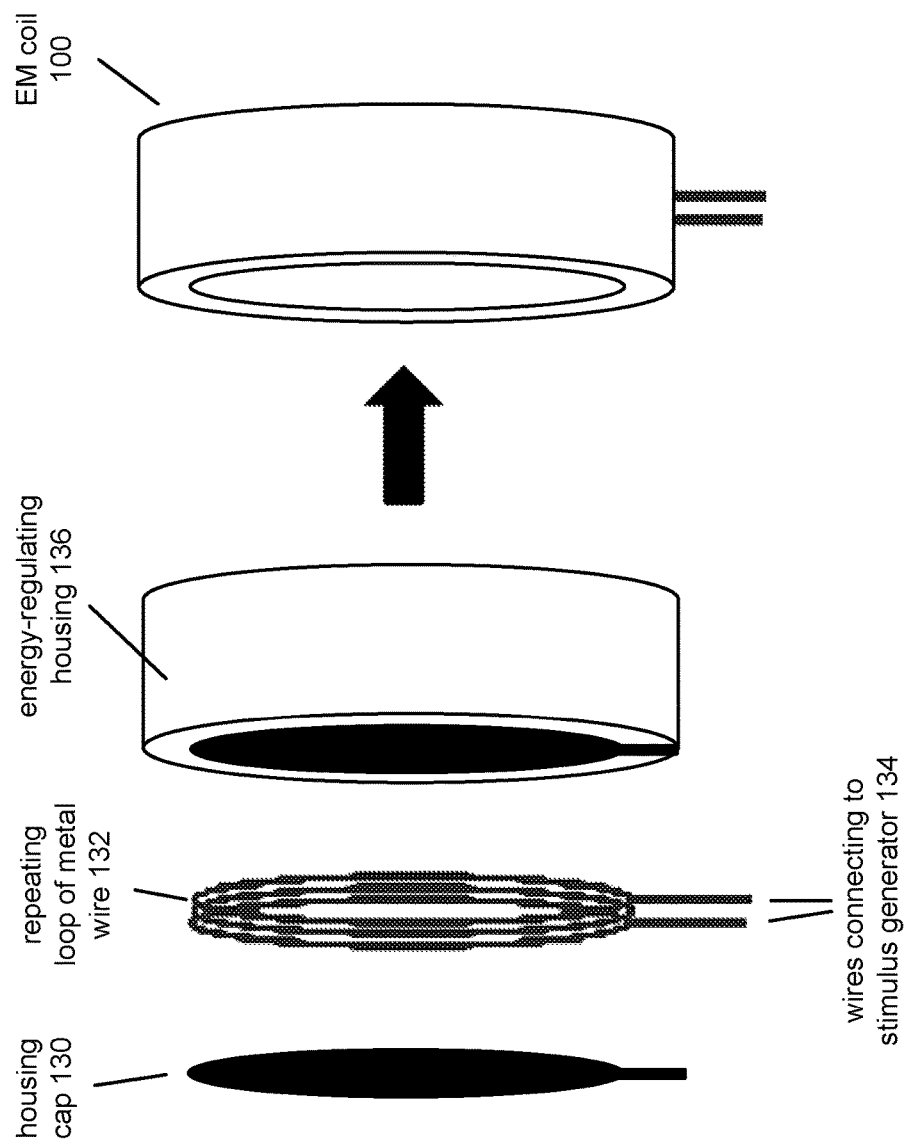
FIG. 1A depicts an exploded view of an electromagnetic (EM) coil composed of an energy-regulating housing, a repeating loop of metal wire (coil), and a housing cap, illustrating the assembly of these components into the closed EM coil.

The skilled artisan will understand that the drawings are for illustration purposes only. The drawings are not intended to limit the scope of the present teachings in any way.

DETAILED DESCRIPTION OF THE INVENTION

Neural Structure Modulation Apparatus

The purpose of stimulation of the facial nerve system by some embodiments of the apparatus is to modulate the cranial blood flow. Cranial blood flow generally includes blood flow to the brain and blood flow to other, non-brain tissues of the head and neck. Modulation of blood flow, such as cranial blood flow, includes increasing, decreasing, redistributing, connecting, or disconnecting various subdivisions thereof, or otherwise changing blood flow, such as to the cerebral, carotid, and/or extracerebral arteries, including but not limited to the arteries of the brain, brainstem, meninges, face, scalp, head and neck soft tissues, ears, and eyes of a mammalian subject. As used herein, the term "mammalian subject", "subject", or "patient" refers to any mammal, including humans. The term "facial nerve system" as used herein includes, but is not limited to, the facial nerve, the entry region of the facial nerve into the internal auditory canal/internal acoustic meatus, the geniculate ganglion, the tympanic plexus, paratympanic organ(s), the intermediate nerve (of Wrisberg), the pterygopalatine/sphenopalatine nerves and ganglion, the petrosal nerves, the ethmoidal nerves, the palatine nerves, the vidian nerve, the sensory and motor fibers of any of the aforementioned structures, fibers of passage through the aforementioned structures, the communicating branches and connections of the aforementioned structures, and the communicating branches and connections between the aforementioned structures and the ophthalmic, trigeminal, glossopharyngeal, cervical, or vagal nerves. These components of the facial nerve system are in the vicinity of, in proximity to, or are proximate to the ear.

In some embodiments, the apparatus stimulates the facial nerve system in order to increase blood flow to the brain of the subject for treatment of an ischemic stroke, to enhance delivery of a blood-borne pharmacologic agent to treat a condition of the subject, or to dilate arteries for the purpose of allowing passage of an endovascular catheter. In other embodiments, blood flow to the brain or other parts of the head is decreased by stimulation. As used herein, the term "stroke" refers to any type of stroke, and the phrase "stroke caused by atherosclerotic disease" refers specifically to stroke caused by atherosclerotic disease involving the cerebral arteries, which includes about 20% of all stroke. As used herein, the term "condition" refers to any condition for which increase (or reduction in some instances) of blood flow provides treatment or some alleviation of the pathophysiology, signs, or symptoms.

Other disease of abnormal blood flow to the brain may similarly benefit from facial nerve system stimulation. For example, regular facial nerve stimulation may improve blood flow in conditions of dementia or head trauma. As another example, facial nerve stimulation may reduce blood flow in cases of brain tumor, headache, or other hyperemic diseases. Additionally, stimulation of the facial nerve system may offer benefit in disorders of cerebral excitability, such as epilepsy and seizure disorders. Alternatively, stimulation of the facial nerve system may be used to treat disorders of the eye or ear, including those related to blood flow or pressure in those structures. In some embodiments used for these conditions, the orientation of various portions of the apparatus may be adjusted and/or the stimulation parameters may be adjusted to achieve the desired effect or benefit. In some embodiments used for these conditions, the orientation of the apparatus and the stimulation parameters employed are the same as those used for stroke.

As mentioned above, in some cases, stimulation of the facial nerve in hemorrhagic stroke patients may not dilate the arteries of the brain and/or head, but may cause constriction of the arteries supplying the brain and/or head, reducing the likelihood of additional hemorrhage from the site of arterial rupture. Preclinical/animal studies of subarachnoid hemorrhage and intracerebral hemorrhage performed in association with the invention have shown that hematomas from these hemorrhages, once stable in size, do not enlarge after stimulation of the facial nerve using stimulation parameters that are otherwise effective at increasing cerebral blood flow in ischemic stroke.

In ischemic stroke, it has been demonstrated that facial nerve stimulation performed in association with the invention improves blood flow to the brain and also increases blood flow to the tissues of the head outside of the skull. In contrast, in hemorrhagic stroke, stimulation of the facial nerve does not appear to significantly increase blood flow to the brain, and it reduces blood flow to the tissues of the head outside of the skull. Thus, most of the embodiments of the device described herein are intended to be applied to a stroke subject without knowing if the subject has an ischemic or hemorrhagic stroke ('undifferentiated' stroke). In this use, the device may provide benefits to the subject, or it may only provide benefit to those subjects with ischemic stroke while doing no harm to those subjects with hemorrhagic stroke.

This property of the facial nerve, i.e., to withhold dilating cranial arteries and increasing cranial blood flow, in the condition of hemorrhagic stroke may reflect sensitivity to blood products, elevated intracranial pressure, or other properties of the hemorrhagic stroke. This property of the facial nerve may in part be mediated by additional neural structures including but not limited to sensory branches of the ophthalmic, trigeminal, glossopharyngeal, cervical, or vagus nerves, or by the circumventricular organs of the brain.

FIG. 1A depicts an embodiment of the device in which an electrode or electrically-conductive element, in this case repeating loops of metal wire 132, is housed in an energy-regulating housing 136 so as to form an electromagnetic (EM) coil 100. Placement of the repeating loops metal wire 132 inside the hollow lumen of the energy-regulating housing 136 allows for the egress of wires connecting to the stimulus generator 134. The repeating loops of metal wire 132 are closed inside the hollow lumen of the energy-regulating housing 136 by a housing cap 130.

In some embodiments of the apparatus, the energy-regulating housing is composed of two or more materials with different heat conductivities. The energy-regulating housing that touches, faces, or approximates the patient is composed of a material that has a low thermal conductivity whereas all other sides (including the side facing away from the patient) has a high thermal conductivity. The general purpose of this is to direct heat flow from the electrically-conductive elements away from the patient.

Figure 1B:
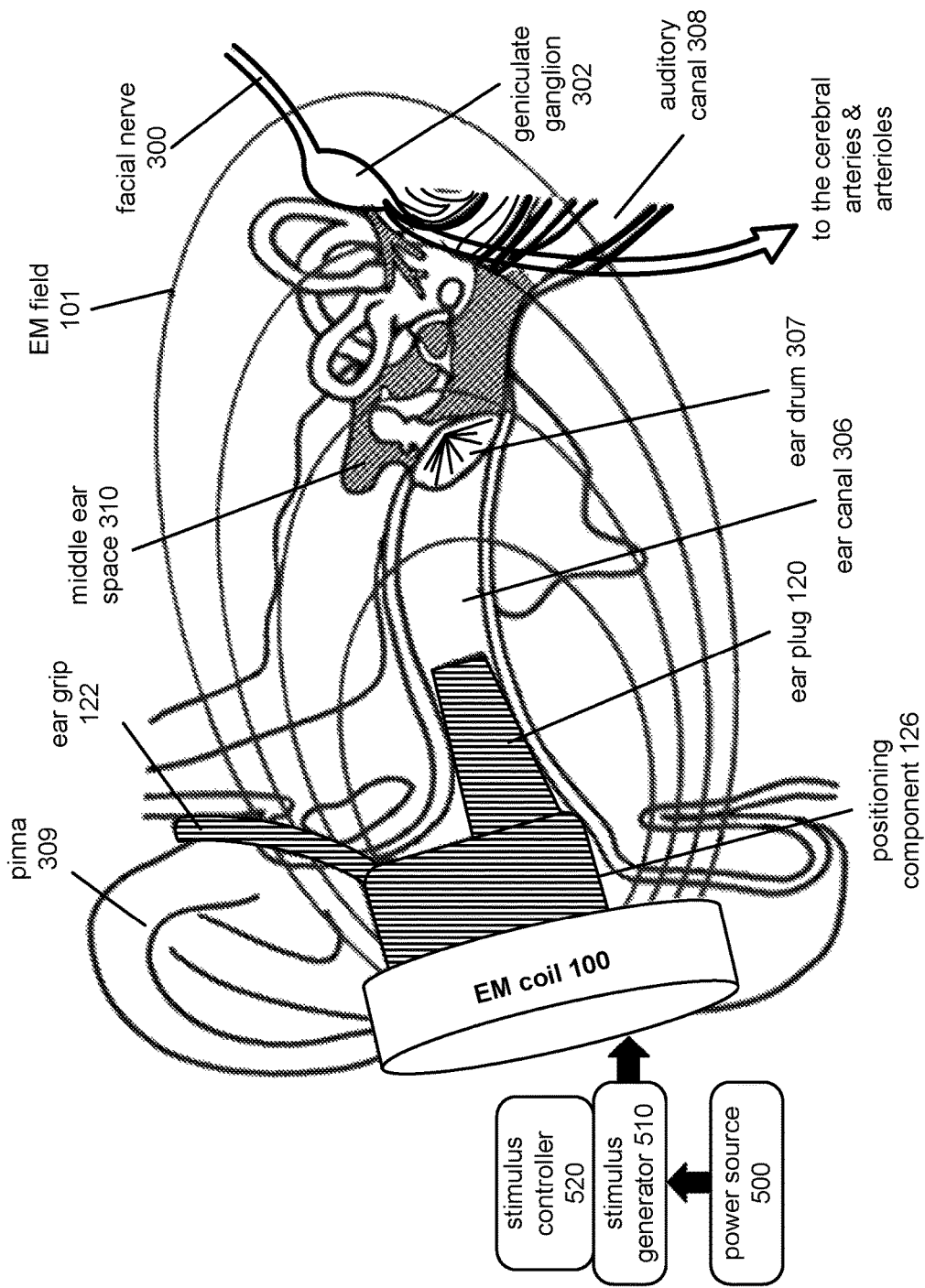
FIG. 1B depicts a cross section of the ear including external, middle, and inner ear structures and surrounding structures, and the Figure illustrates the positioning of an EM coil using positioning components (e.g., an ear plug) so that the stimulus energy (e.g., EM field) is directed at a part of the facial nerve system, in this example the geniculate ganglion.

FIG. 1B illustrates various components of the ear, including the pinna 309, ear canal 306, middle ear space 310, and auditory canal 308. As used herein, the term "ear" refers to any portion of the ear, including the external, middle, and inner ear, unless otherwise specified, to the general region of the head where those structures are found, or to the region of the temporal bone housing auditory, vestibular, and other neural structures. In some embodiments, the apparatus stimulates components of the facial nerve system that pass through, have a portion or branch within, or contribute to a structure within the middle ear 310. Furthermore, in some embodiments, the apparatus stimulates components of the facial nerve system that are immediately outside the middle ear 310. As used herein, the term "limited facial nerve system" includes the nerves and neural structures listed above, but not including the sphenopalatine nerves and ganglion, the petrosal nerves and communicating branches thereof, the ethmoidal nerves and communicating branches thereof, the palatine nerves including nasopalatine nerves, the vidian nerve and communicating branches thereof, and communicating branches between any of the aforementioned structures and the trigeminal nerve system. The apparatus is described throughout as one that is used in association with the ear, but the apparatus can also be positioned elsewhere on the head or other location that permits the apparatus to stimulate the facial nerve system. Similarly, the apparatus can also be used for stimulation of other neural systems. As used herein, the term "neural system" refers to any nervous tissue in the body of a subject FIG. 1B depicts an embodiment of the device in which the EM coil 100 is placed against the surface of the head near the ear. Throughout this description, the term "EM coil" is used, but this can also refer to other types of electrodes or electrically conductive elements in the embodiments described. The EM coil 100 is held against the surface of the head by an ear grip 122 that reaches behind the pinna 309 of the external ear (though other ear grip designs or mechanisms for ear or head attachment can also be used), and is positioned by an ear plug 120 that is inserted into the ear canal 306 and a positioning component 126 that is interposed between the ear plug 120 and the EM coil 100 (though other mechanisms for positioning can also be used). The ear plug 120 and positioning component 126 serve to orient the EM coil 100 such that the EM field 101 generated by the EM coil 100 is directed at the facial nerve 300 or at a part of the facial nerve system such as the geniculate ganglion 302.

Continuing with FIG. 1B, in some embodiments, the positioning component 126 is formed of a substantially rigid material. In some embodiments, the positioning component 126 is formed from a substantially flexible material. In some embodiments, the shape of the positioning component 126 can be adjusted to alter the orientation of the EM field 101 generated by the EM coil 100.

In some embodiments, the apparatus is applied to one side of the head, as shown in FIG. 1B. In other embodiments, the apparatus is applied to both sides of the head, similar in appearance to ear muffs or ear plugs.

FIG. 1B depicts a power source 500 connected by cables to a stimulus generator 510 that provides, gates, directs, shapes, or otherwise delivers the electrical energy to the EM coil 100 in a manner that allows for generation of the EM field 101. The power source may also be in electrical communication with the stimulus generator with cables as shown or wirelessly. This is true for all embodiments of the power source and stimulus generator described herein. Similarly, the stimulus generator 510 may be in electrical communication with the EM coil 100 by wires or wirelessly, which is true for all embodiments described herein. The power source 500 provides the electrical current to the stimulus generator 510, which powers the EM coil 100.

As shown in FIG. 1B, in some embodiments, the apparatus further includes a stimulation controller 520 attached to the stimulus generator 510 for adjusting, defining, modulating, or otherwise determining the electrical current applied to the EM coil 100 or controlling one or more settings of the stimulus generator 510. The stimulus controller 520 can include a user interface by which the operator of the apparatus can provide instructions to, or otherwise interact with, the apparatus. The stimulus controller 520 can allow the operator to control the strength, frequency, duration of application, and/or other parameters of the stimulus energy. For example, the stimulus controller 520 can include particular controls (e.g., knobs, digital settings, etc) for increasing or decreasing the strength of the electrical current and controlling various other factors or parameters in the operation of the apparatus. Where the apparatus is connectable to a computer or other machinery, the operator may also be able to interact with and control the apparatus via the interface of the computer, including tracking the subject's vital signs, responses to the stimulus energy over time, machinery performance, and so forth.

The stimulus controller 520 can further be used to adjust the stimulus energy for various purposes. For example, the stimulus energy can be adjusted based on one or more physiological or pathophysiological responses of the subject to the stimulus energy (e.g., carotid artery blood flow; cerebral artery blood flow; blood flow to the central nervous system; facial nerve electrical potentials; skin/scalp galvanic responses; skin/scalp blood flow; ear temperature; pupilometry; intraocular pressure; blood flow to the eye; bioelectric potentials; electroencephalogram waveforms; electrophysiological testing of the auditory or vestibular systems; taste sensation; audition; lacrimation; nasal drainage; nasal congestion; salivation; sound sensitivity; face, head, or hand movements or electromyographic potentials; speech production or arrest; sensation of body movement; eye movements; cranial blood flow; direct or indirect activity of a nerve; and severity of neurological dysfunction of the subject). For example, if the subject exhibits certain eye movements, the operator can observe this and respond to this by changing the stimulus energy or certain other parameters associated with the stimulus energy. As another example, the stimulus energy can be adjusted to increase or otherwise control blood flow to the brain of the subject as either the direct treatment of a disease process or else to facilitate the delivery of blood-borne pharmacologic agents as the treatment of a disease process. As another example, the time since the onset of stroke symptoms may inform the stimulus controller 520 to allow the stimulus generator 510 to deliver stimulation energy of certain characteristics or duration. As another example, signal provided to the stimulus controller 520 representing physiological or pathophysiological responses of the subject may direct the stimulus controller 520 to adjust the shape of a positioning component 126. In some embodiments, the operator is replaced by a servocontrol or automatic control mechanism that can detect one or more physiological or pathophysiological responses of the subject to the stimulus energy.

The apparatus of FIG. 1B can be a chronic/repeated treatment device or can be an acute/single treatment device. For acute treatment of a condition, the apparatus of FIG. 1B can be placed on the subject's ear, and can deliver stimulus energy as desired by a physician or other operator. The stimulus generator 510 can be attached to a stimulus controller 520 that allows a physician or other operator to control when the stimulus energy is delivered, the intensity of the stimulus energy, etc. For chronic treatment or prevention of a condition, the apparatus of FIG. 1B can be worn as a chronic treatment device that is worn continuously or regularly by the subject. It can be worn all the time, at certain times of day, or whenever prescribed. As one example in which chronic treatment is useful, atherosclerotic disease of the cerebral arteries narrows cerebral arteries, which may chronically impair blood flow to parts of the brain, thereby causing among other symptoms recurring near-strokes/transient ischemic attacks as blood flow becomes intermittently compromised. In order to overcome the narrowing in the cerebral arteries caused by atherosclerosis or other malformations, repeated stimulation of the facial nerve system provided by a chronic treatment device can be used to maintain dilation of the arteries, thereby preventing stroke caused by atherosclerotic disease. The apparatus of FIG. 1B can thus chronically stimulate or modulate one or more components of the facial nerve system in the vicinity of the ear to treat stroke or other conditions.

In some embodiments, the EM coil 100 is between 2 cm and 8 cm in diameter. In some embodiments, the EM coil 100 is a hollow "doughnut" shape. In some embodiments that include repeating loops of wire, the more central loops of wire are progressively raised off the plane of the largest loop so as to form a substantially cone-like shape wherein the apex of the cone is inserted into the ear canal.

In some embodiments, the ear plug 120 is formed from a sound-dampening material. In some embodiments, the ear plug 120 and/or positioning component 126 are formed from heat-adsorbent or heat-resistant materials. In some embodiments, the position of the ear plug 120 and/or positioning component 126 relative to the EM coil 100 offsets the EM coil 100 from a position immediately over the ear canal for the purpose of directing, focusing, or otherwise changing the use of the EM field 101.

Placement of the stimulator against the external ear may be performed, guided, or assisted with various accessory devices such as the positioning component 126 of FIG. 1B that are of different or customized geometric shape (such as wedges) for the purpose of orienting the EM coil 100 in a manner that effectively stimulates the facial nerve system or select components of the facial nerve system. Such accessory devices may relate to facial or cranial anatomy, external ear anatomy, and/or ear canal anatomy. In some embodiments, such accessory devices may be adjusted or formed based on neuroimaging of the facial nerve system, the location of select components of the facial nerve system such as the geniculate ganglion, the bony structures that house the facial nerve system, and/or other nearby structures. In some embodiments, such accessory devices may be adjusted based on the length, width, height, circumference, or other external measures of the head and/or neck of the subject. In some embodiments, such accessory devices may be adjusted based on feedback from a sensor device.

Figure 2:
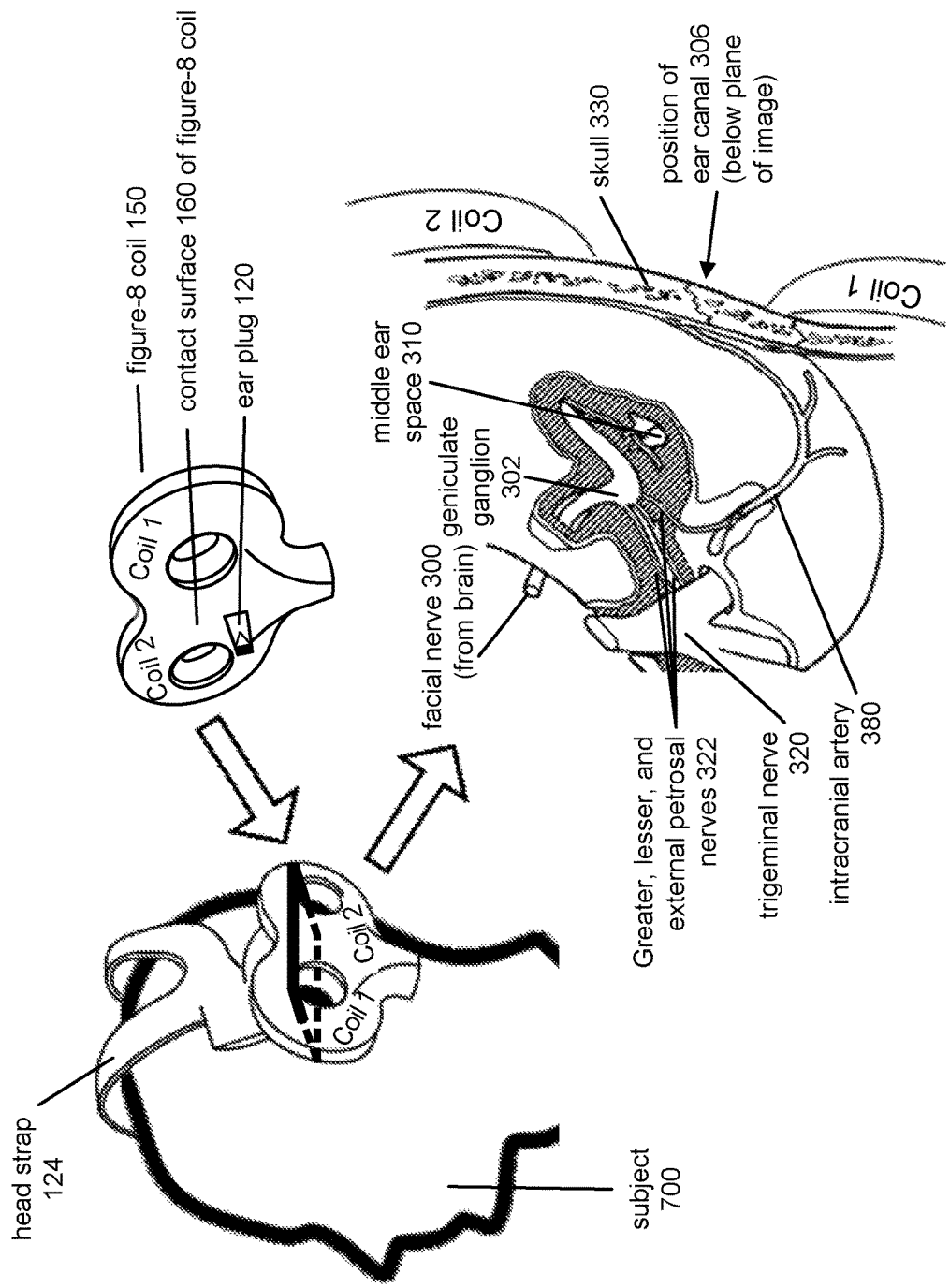
FIG. 2 depicts two EM coils in a figure-8 coil design held against the side of the head by a head strap so that the EM coils are positioned on opposite sides of the head by an ear plug attached to the EM coil housing, for the purpose of focusing the EM field on a part of the facial nerve system (in this example the geniculate ganglion).

FIG. 2 depicts an embodiment in which multiple electrodes or electrically-conductive elements, in this case EM coils, are arranged in a geometric shape and applied to the surface of the head in the vicinity of the ear for the purpose of stimulating the facial nerve system or a portion of the facial nerve system. In this embodiment, two circular EM coils are placed side-by-side so as to form a figure-8 coil 150, and an ear plug 120 is placed upon the contact surface 160 of the figure-8 coil. The position of the ear plug 120 on the surface of the figure-8 coil 150 is determined so that the juncture of the two coils of the figure-8 coil 150 is placed over the ear canal 306 when the contact surface 160 of the figure-8 coil 150 is placed in position on a subject 700. In some embodiments, the housing for the figure-8 coil 150 is made of a substantially flexible material that allows adjustment of the separation and/or angulation of the two EM coils. In other embodiments, the EM coils (as shown in element 100 of FIG. 1B) of the figure-8 coil 150 are contained in separate housings. In some embodiments, a positioning component is placed or can be placed between the ear plug 120 and the figure-8 coil 150. The housing for the figure-8 coil 150 can also be an energy-regulating housing capable of electrically insulating the electrically-conductive element and dissipating heat from the apparatus in a desired manner.

FIG. 2 illustrates the relationship between the two EM coils and underlying structures including the middle ear space 310, facial nerve 300, geniculate ganglion 302, branches of the geniculate ganglion (including but not limited to the greater, lesser, and external petrosal nerves 322), trigeminal nerve 320, and intracranial arteries 380 (including cerebral, meningeal, and other arteries).

Figure 3:
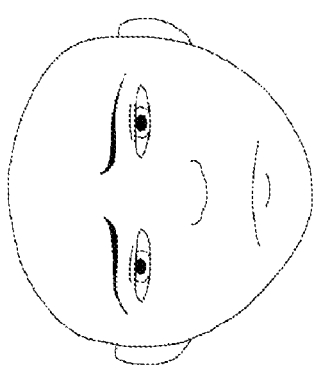
FIG. 3 depicts the figure-8 coil design shown in FIG. 2, in which the two EM coils are kept in an adjustable housing that allows for separation and angulation of the EM coils according to head size and shape.
Figure 3:
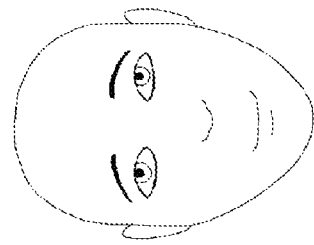
Figure 3:
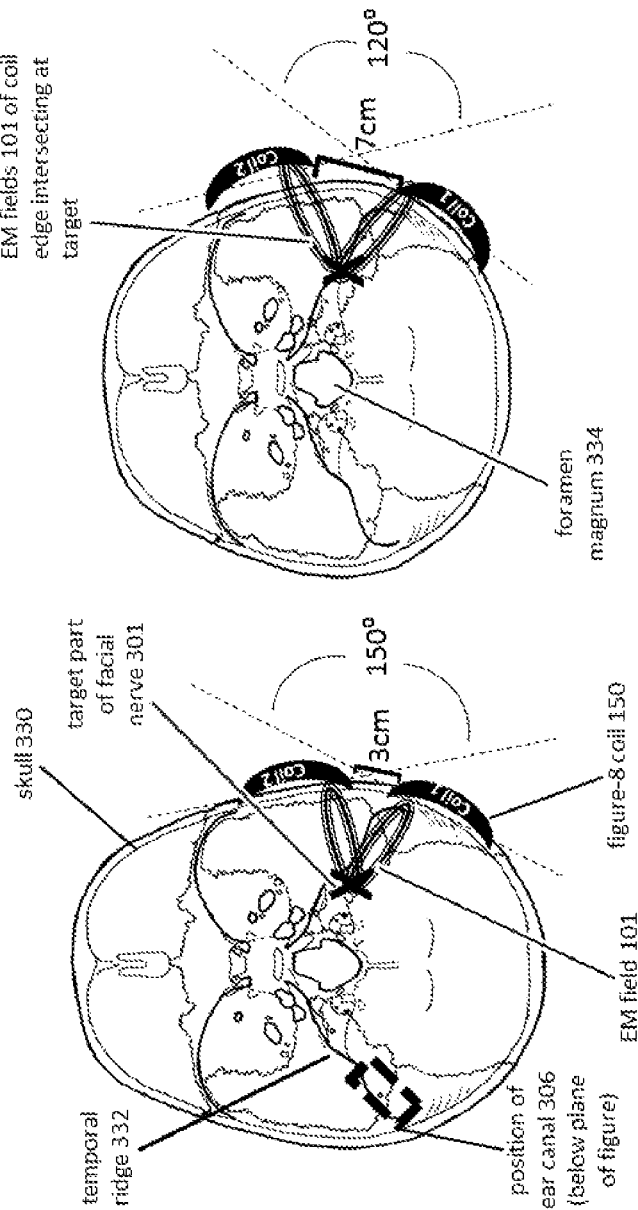

Continuing from FIG. 2, then, FIG. 3 depicts the manner in which the two EM coils of the figure-8 coil 150 can be angulated and/or separated to accommodate different head sizes and shapes so as to allow for the intersection of the two EM fields, producing a summation or focusing of stimulation intensity at the desired region of the facial nerve system. FIG. 3 illustrates the shape of the skull 330 in a subject with a thin head 342 and in a subject with a round head 344. The skull 330 from each head has been opened with an axial cut in these images and the brain removed to show the base of the skull, including the foramen magnum 334 through which the spinal cord enters the skull and fuses with the brainstem, and the temporal ridge 332/petrous portion of temporal bone that contains in it the ear canal 306, middle ear space, and inner ear structures. When applied to the thin head 342, the figure-8 coil 150 as described above will assume a shape in which the two EM coils are closely spaced and/or obtusely angled. In comparison, when applied to the round head 344 as described above, the figure-8 coil 150 will assume a shape in which the two EM coils are more widely separated and/or acutely angled. By adjusting the separation and/or angulation between the two EM coils of the figure-8 coil 150, the EM fields 101 generated by the opposing edges of the two EM coils will focus on the desired target part of the facial nerve 301. In some embodiments, the angulation and/or separation between the two EM coils are in part determined by a mechanical apparatus contained within the substantially flexible housing of the figure-8 coil 150 that restricts movement of the two EM coils. In some embodiments, the mechanical apparatus that restricts the angulation and/or separation of the EM coils 100 is external to the housings for the EM coils and connects the separate housings together in the general form of a figure-8 coil 150. In other embodiments, the angulation and/or separation of the two EM coils are in part determined by additional anatomical landmarks of the head and/or neck.

Figure 4:
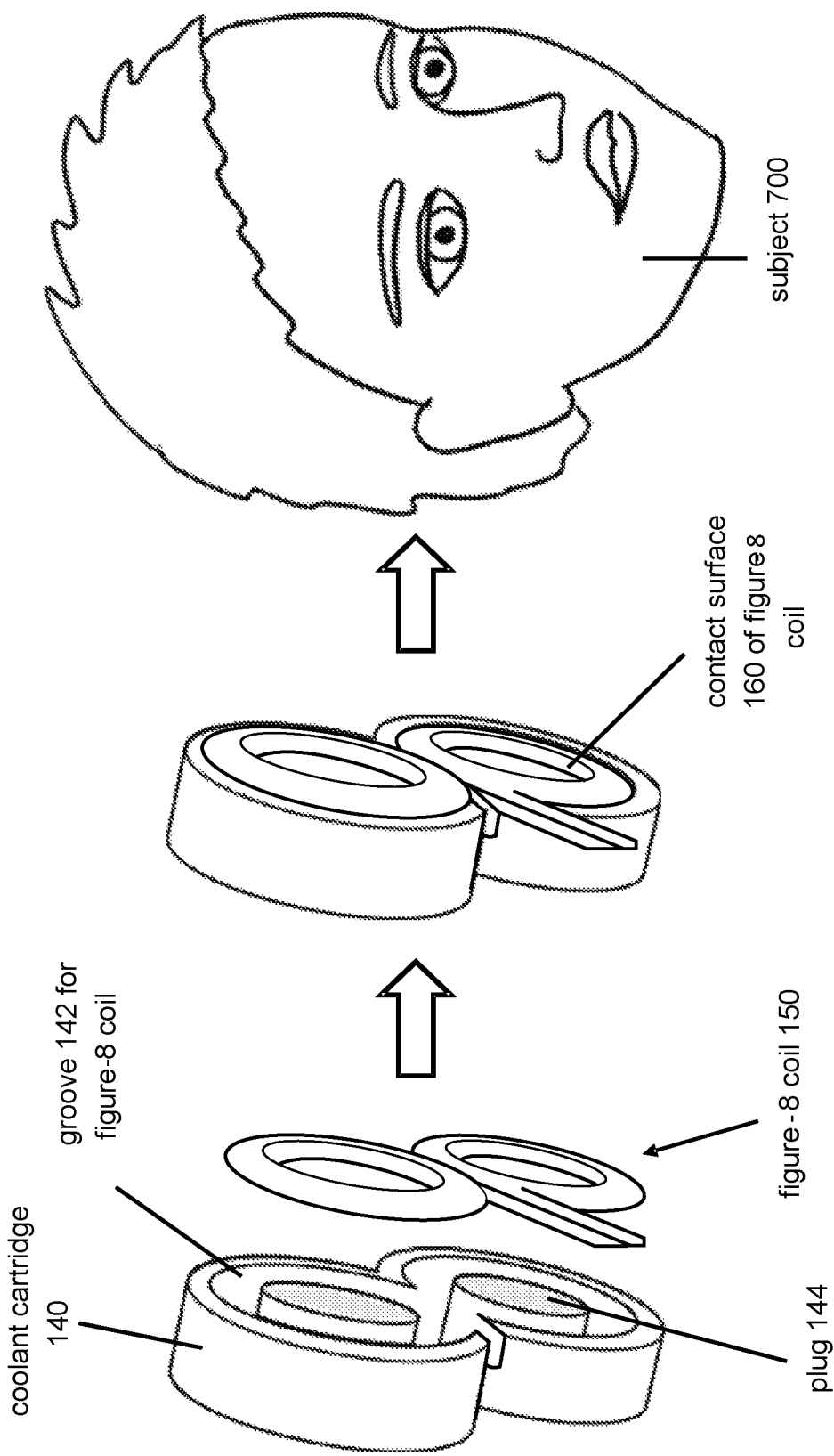
FIG. 4 depicts a coolant cartridge shaped to accept a figure-8 coil into a groove on one surface, thereby leaving only a single face of the figure-8 coil exposed for application to the side of the head of a subject.

FIG. 4 depicts an apparatus for reducing the temperature of an EM coil, here represented by an embodiment of a figure-8 coil 150. In this apparatus, a case, such as coolant cartridge 140, composed of an external container form-fitted to the figure-8 coil 150 by means of a groove 142 on one surface is placed upon the figure-8 coil 150. Because in this embodiment the figure-8 coil 150 has a hollow central region within each of its two EM coils, the coolant cartridge 140 is shaped so as to have two plugs 144 that fill the hollow concentric regions of the two EM coils when the figure-8 coil 150 is placed into the groove 142 of the coolant cartridge 140. This general configuration allows for maximum surface-to-surface contact between the figure-8 coil 150 and the coolant cartridge 140, thereby maximizing heat transfer from the figure-8 coil 150 to the coolant cartridge 140 while not obstructing the contact surface 160 of the figure-8 coil 150 that is to be directly or otherwise closely applied to the external surface of a subject 700 such as the vicinity of the ear. The coolant cartridge 140 can include a number of components (e.g., materials, compounds, or devices) that absorb or dissipate heat. In some embodiments, the coolant cartridge 140 contains a phase-change material. In some embodiments, the phase-change material is a hydrated salt. In some embodiments, the coolant cartridge 140 or its contents undergo an irreversible change during heat absorption. In some embodiments, the coolant cartridge 140 contains a component that allows for electrical current to flow through the EM coil when the component combines with, connects to, or contacts an aspect of the EM coil, acting as a 'fail safe' switch to ensure connection of the coolant cartridge 140 and EM coil. In some embodiments, the 'fail safe' switch is destroyed after a single combination, connection, or contact between the coolant cartridge 140 and the EM coil. In some embodiments, the coolant cartridge is a separate structure from the rest of the apparatus and in other embodiments it is integrated with the apparatus. The energy regulating housing can also include a coolant cartridge or components for modulating the temperature of the apparatus.

Figure 5:
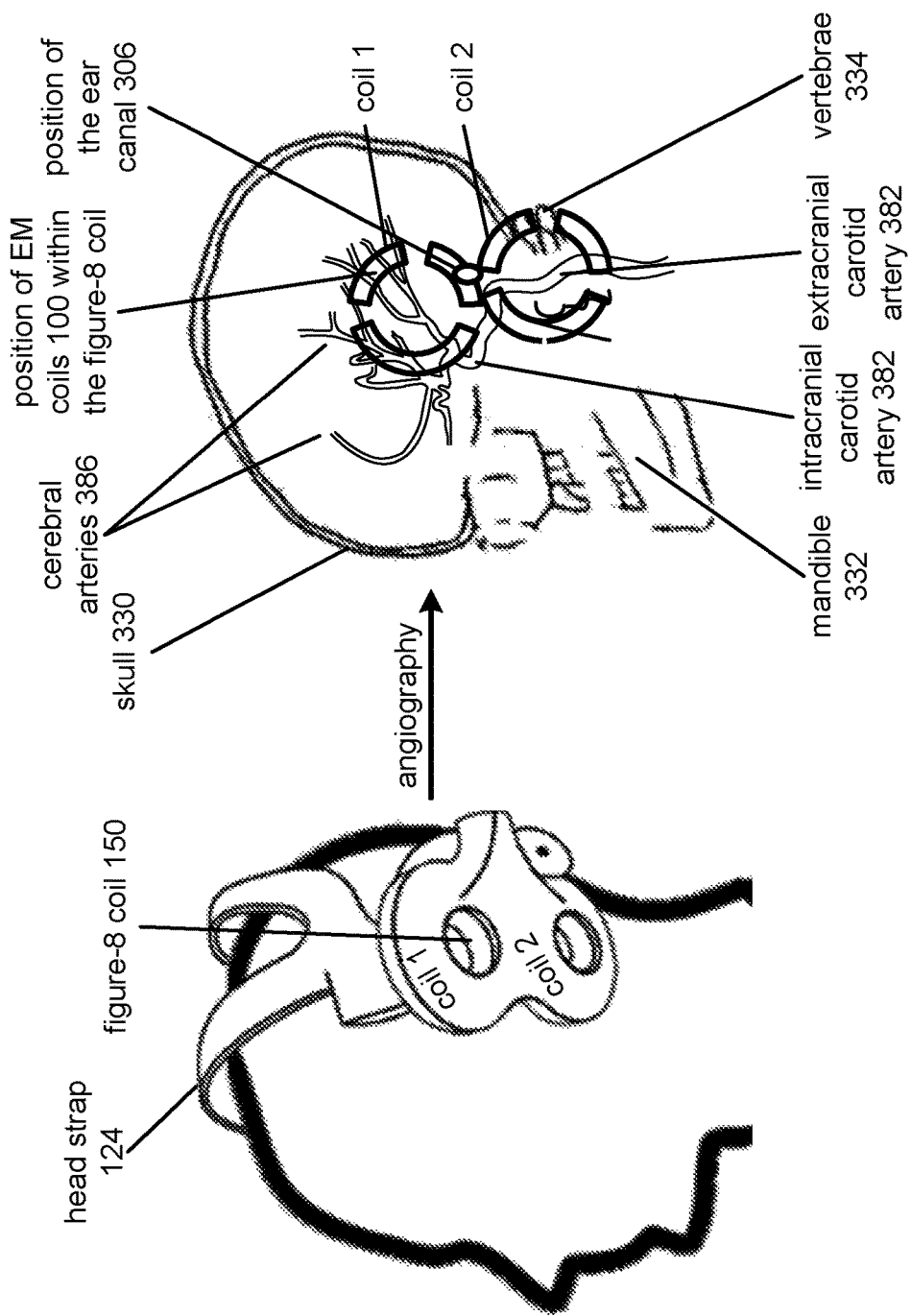
FIG. 5 depicts the two coils of a figure-8 coil oriented vertically so as to position the lower coil substantially over the internal carotid artery and the upper coil over the intracranial arteries, for the purpose of measuring blood flow in the intracranial arteries.

FIG. 5 demonstrates an apparatus intended for stimulation of the facial nerve, facial nerve system, or part thereof, which is also designed for the purpose of measuring blood flow in the vicinity of the EM coils. In some embodiments, the EM coils of the apparatus are also employed for the purpose of measuring blood flow. In some embodiments, two EM coils 100 arranged as a figure-8 coil 150 are placed over the ear by means of attachment to a head strap 124 that orients the two coils in a substantially vertical manner. In some embodiments, this position is also determined by an ear plug or similar device attached to the subject side/contact surface of the figure-8 coil 150 that uses the ear or part thereof as an anatomical landmark. When the EM coils 100 are not receiving electrical current for the purpose of generating an EM field to stimulate neural structures, they are controlled independently by a sensor device (not shown) that delivers, or instructs the stimulus generator to deliver, electrical current to the lower of the two EM coils 100 (in this example, Coil 2) so as to generate an EM field, thereby providing a magnetic label to blood as it passes through the underlying extracranial carotid artery 384. The sensor device is able to receive and interpret an electrical current provided by the upper of the two EM coils 100 (in this example, Coil 1) that reflects the release or decay of energy from the magnetized blood, or that detects the magnetic property of the blood, in the intracranial carotid artery 384 and/or cerebral arteries 386, thereby reflecting movement of labeled blood from the extracranial carotid artery 384 into the intracranial carotid artery 382 and/or cerebral arteries 386. The sensor device is capable of interpreting the electrical current provided by the upper of the two EM coils 100 to provide a blood flow measure of either absolute or relative units. In some embodiments, the sensor device is capable of separating multiple blood flow signals in a manner based on the depth-of-origin of the release or decay of magnetic energy of the blood and/or based on the magnitude of the release or decay of magnetic energy of blood. In some embodiments, the plurality of EM coils 100 is oriented to magnetically-label blood in the intracranial carotid artery 382 and detect signal in the intracranial carotid artery 382 and/or cerebral arteries 386. In some embodiments, a single EM coil 100 serves to both magnetically label blood and detect the magnetic label of blood.

In some embodiments, intermittent measurement of blood flow is accomplished by the creation of a uniform magnetic field by an EM coil that is disturbed, disrupted, or otherwise changed by the movement of the blood. In other embodiments, measurement of blood flow may be accomplished by ultrasound, infrared, electrical, optical, microwave, acoustic, mechanical, or other electromagnetic measurements.

Because EM fields can cause heating of metal, or the movement of metal, it may be useful to have a metal detection function as part of the apparatus. In some embodiments (not shown), one or more EM coils used primarily to deliver stimulus energy are employed in a secondary manner to detect metal between the EM coil(s) and the subject, or placed on or implanted in the subject. In these embodiments, one of the EM coils receives and alternating electrical current from the stimulus generator or power source, creating eddy currents in any external metal near the coil. The second EM coil then acts as a magnetometer to detect the eddy current created by the external metal. In some embodiments, the apparatus is equipped with a separate metal detector device.

Multiple EM coils can be assembled into an array for the purpose of combining, shaping, or distorting the EM field in a desirable manner. In some embodiments, the plurality of EM coils is arranged on a single side of the head. In some embodiments, the plurality of EM coils is arranged on both sides of the head in either a symmetric or asymmetric manner. In some embodiments, one or more of the plurality of EM coils is placed in the mouth or under the chin.

Figure 6:
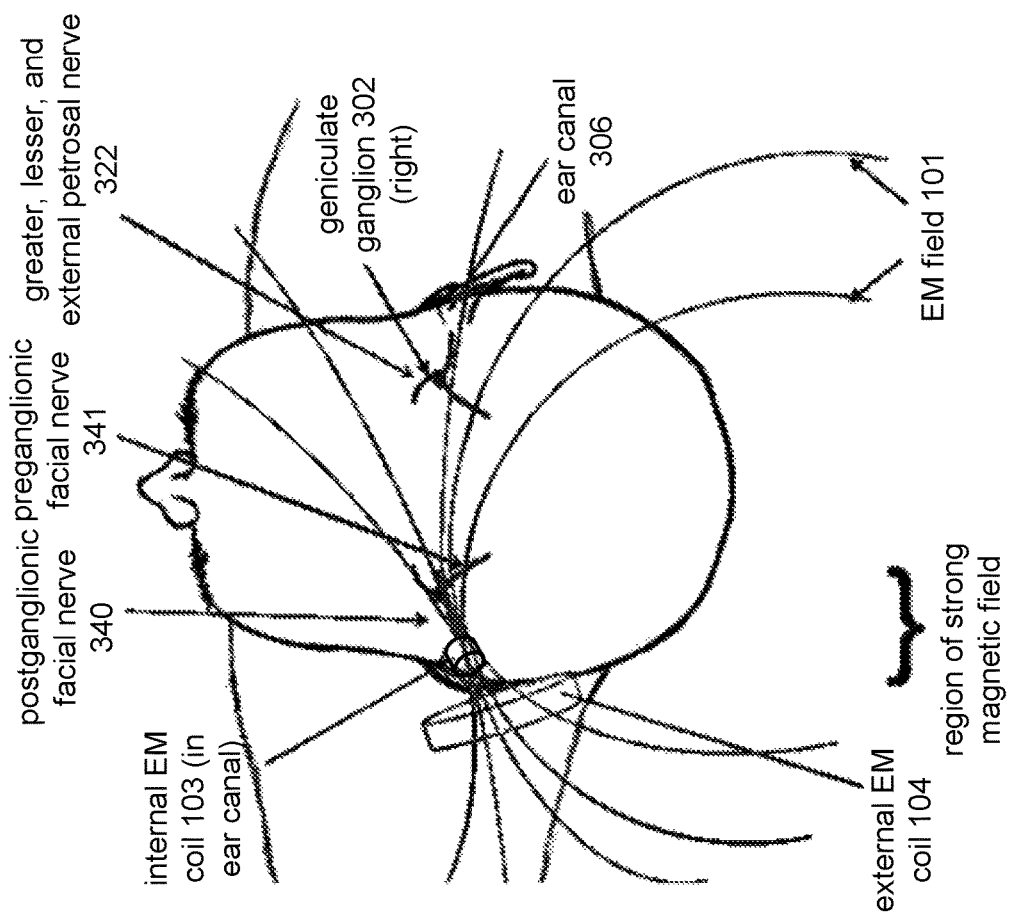
FIG. 6 depicts an assembly of two EM coils applied to one side of the head for unilateral stimulation of the facial nerve system in which a small EM coil is placed in the ear canal and a large EM coil is placed on the side of the head, and in which the two EM coils generate an EM field focused by the small EM coil in the ear canal so as to target a portion of the facial nerve system, in this example the geniculate ganglion.

FIG. 6 depicts an assembly of a plurality of EM coils on one side of the head. In this embodiment, one EM coil is placed in the ear canal 306, serving as an internal EM coil 103. The other EM coil is placed against the side of the head, serving as an external EM coil 104. Electrical current is then delivered to the two EM coils in a manner that is coordinated so as to generate an EM field 101. In some embodiments, the external EM coil 104 serves to provide the majority of the stimulus energy necessary for EM field 101 generation whereas the internal EM coil 103 acts to focus or orient the EM field 101. In some embodiments, the position of the internal EM coil 103 in the ear canal is intended to direct the EM field 101 to a part or portion of the facial nerve on its pre-ganglionic 341 segment or its post-ganglionic 340 segment, wherein the ganglion referred to by the term "ganglionic" is the geniculate ganglion. In some embodiments, the position of the internal EM coil 103 in the ear canal is intended to direct, orient, or guide the EM field 101 at the geniculate ganglion 302 and/or anatomical projections of the geniculate ganglion such as but not limited to the greater, lesser, and external petrosal nerves 322.

Figure 7:
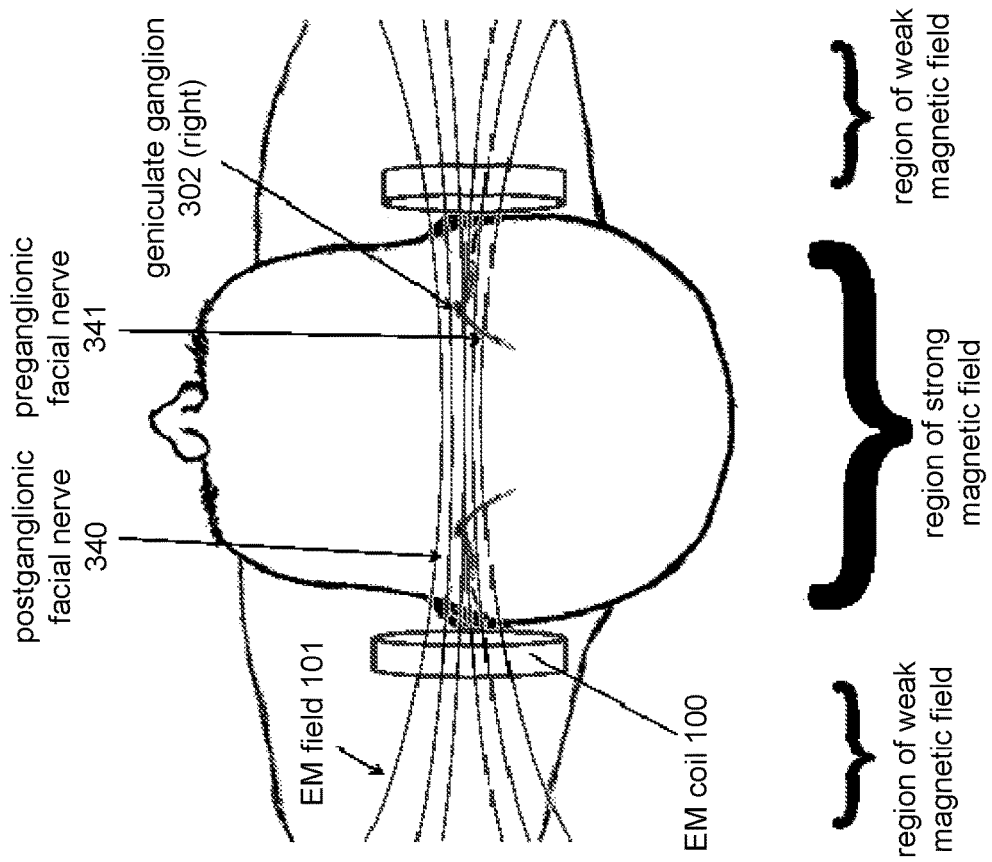
FIG. 7 depicts an assembly of two EM coils in which one EM coil is applied to each side of the head and in which the two EM coils operate in a coordinated manner so as to create an EM field crossing the diameter of the head that stimulates the facial nerve system or components thereof in a bilateral manner.

FIG. 7 depicts a plurality of EM coils arranged on both sides of the head for the purpose of stimulating the facial nerve system bilaterally. In some embodiments, a pair of EM coils 100 is placed over the ear or in the vicinity of the ear in a symmetric manner. Coordinated use of the two EM coils 100 then creates a single EM field 101 that is formed in a substantially linear manner between the two EM coils 100 and that is positioned in such a manner as to stimulate the facial nerve system. In some embodiments, electrical current from a single stimulus generator is alternated between the sets of EM coils on each side of the head by a switch located at the output source of the stimulus generator.

In some embodiments, a portion of the facial nerve system such as the geniculate ganglion 302 is centered in the EM field 101. In some embodiments, one or more parts of the facial nerve between the brainstem and the geniculate ganglion (preganglionic facial nerve 341) are centered in the EM field 101. In some embodiments, one or more parts of the facial nerve between the geniculate ganglion and the stylomastoid foramen (postganlionic facial nerve 340) are centered in the EM field 101. In some embodiments, one or more of the plurality of EM coils receive direct electrical current.

Figure 8A:
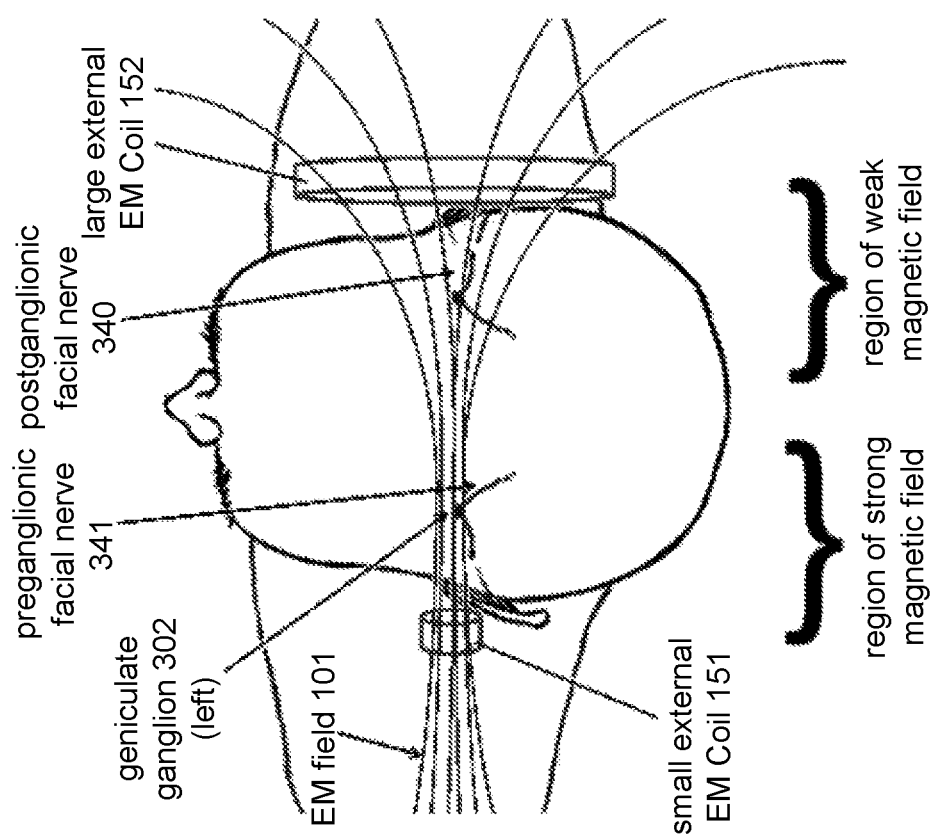
FIG. 8A depicts use of two asymmetric EM coils applied to the side of the head in which a small EM coil serves to condense an EM field generated by a large EM coil placed on the opposite side of the head.
Figure 8B:
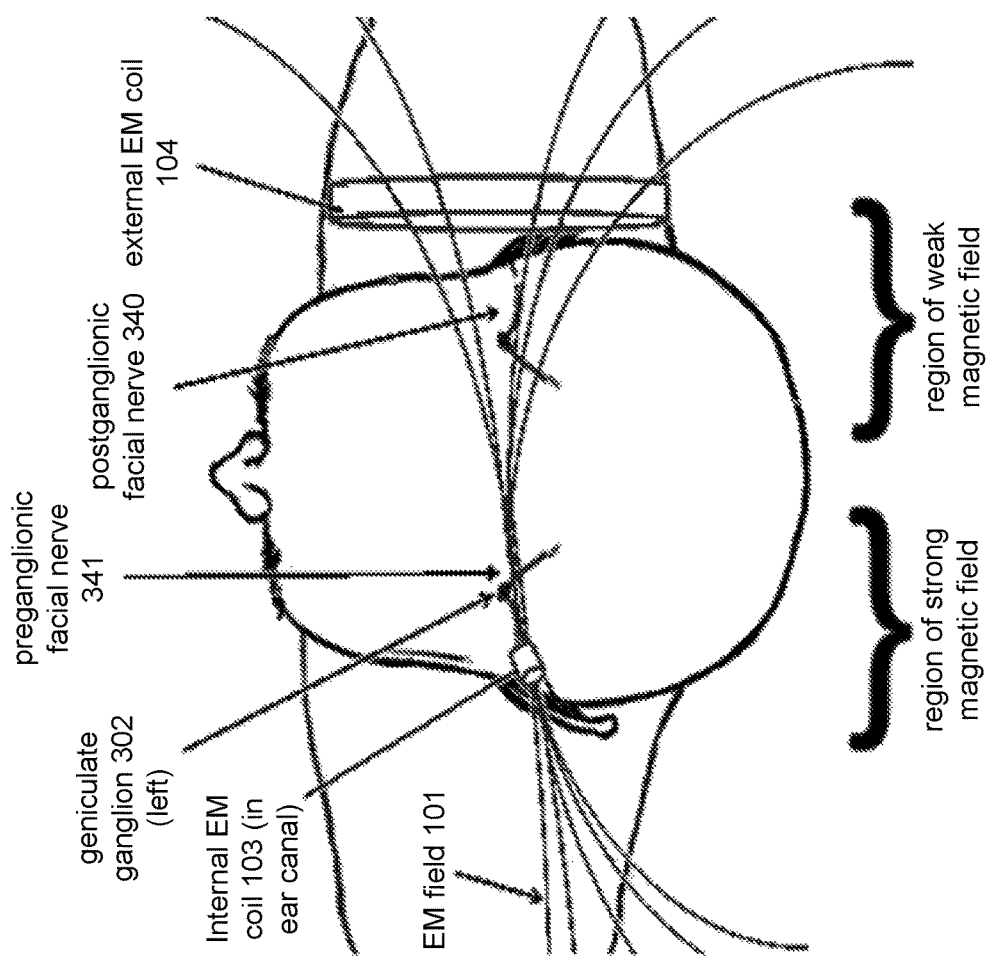
FIG. 8B depicts use of two asymmetric EM coils in which an EM coil placed in the ear canal serves to condense an EM field generated by an EM coil placed on the opposite site of the head.

FIGS. 8A-B depict an array of more than one EM coil arranged on both sides of the head so as to stimulate one or both facial nerve systems. The EM coils are of different sizes, shapes, and/or positions. The purpose of such arrays is to create an EM field 101 that is concentrated or powerful at the site of only one facial nerve system or part thereof. In some embodiments, electrical current is then delivered to the two EM coils in a manner that generate an EM field 101 between the two coils that is substantially asymmetric. As shown in FIG. 8A, in some embodiments, a small external EM coil 151 is placed against the side of the head on one side of the head, whereas a large external EM coil 152 is placed against the other side of the head. As shown in FIG. 8B, in some embodiments, one EM coil is sufficiently sized and shaped to allow for its insertion into the ear canal (internal EM coil 103). In some embodiments, the EM coils are of different sizes and/or shapes.

Figure 9:
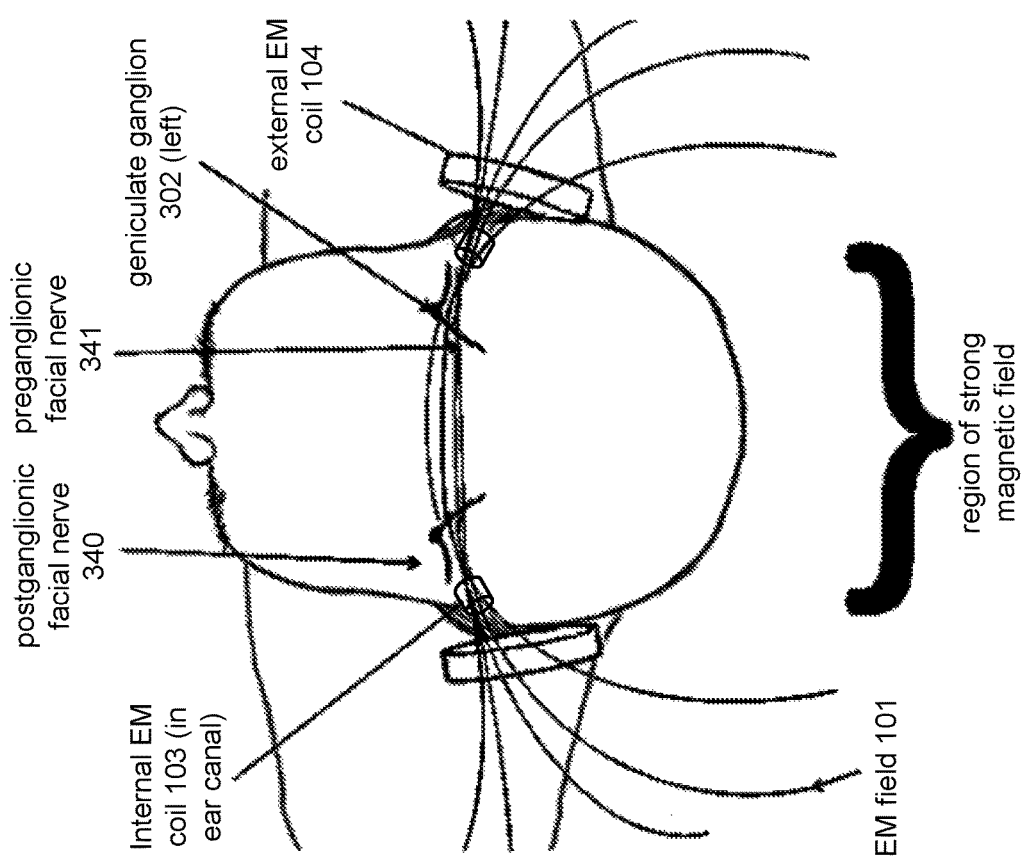
FIG. 9 depicts two pairs of EM coils applied bilaterally to the head, in which each pair is composed of an internal EM coil placed into the ear canal and an external EM coil placed against the side of the head, and in which the two pairs of EM coils operate in a coordinated manner so as to create an EM field across the diameter of the head that stimulates the facial nerve system in a bilateral manner.

FIG. 9 depicts an array of coils (e.g., a plurality or multiple coils) arranged symmetrically on both sides of the head so as to stimulate one or both facial nerve systems in which the EM coils are of different sizes, shapes, and/or positions. The purpose of such arrays is to create an EM field 101 that is of maximal strength at positions of the target segment of the facial nerve system such as the geniculate ganglion 302, preganglionic facial nerve 341, and/or postganglionic facial nerve 340. In some embodiments, the EM coils are divided into pairs, in which a pair of EM coils is placed on each side of the head. In some embodiments, one EM coil of each pair of EM coils is an internal EM coil 103 that is placed in the ear canal, and the other EM coil in the pair of EM coils is an external EM coil 104 placed against the side of the head. In some embodiments, the physical or spatial relationship of the internal EM coil 103 and external EM coil 104 is fixed by a substantially rigid housing. In some embodiments, the two pairs of EM coils on each side of the head are connected to a single stimulus generator that discharges electrical energy into each EM coil of a pair of EM coils, or into each pair of EM coils, in a coordinated manner that can be simultaneous or alternating, and that may be directed by a stimulus controller.

Figure 10A:
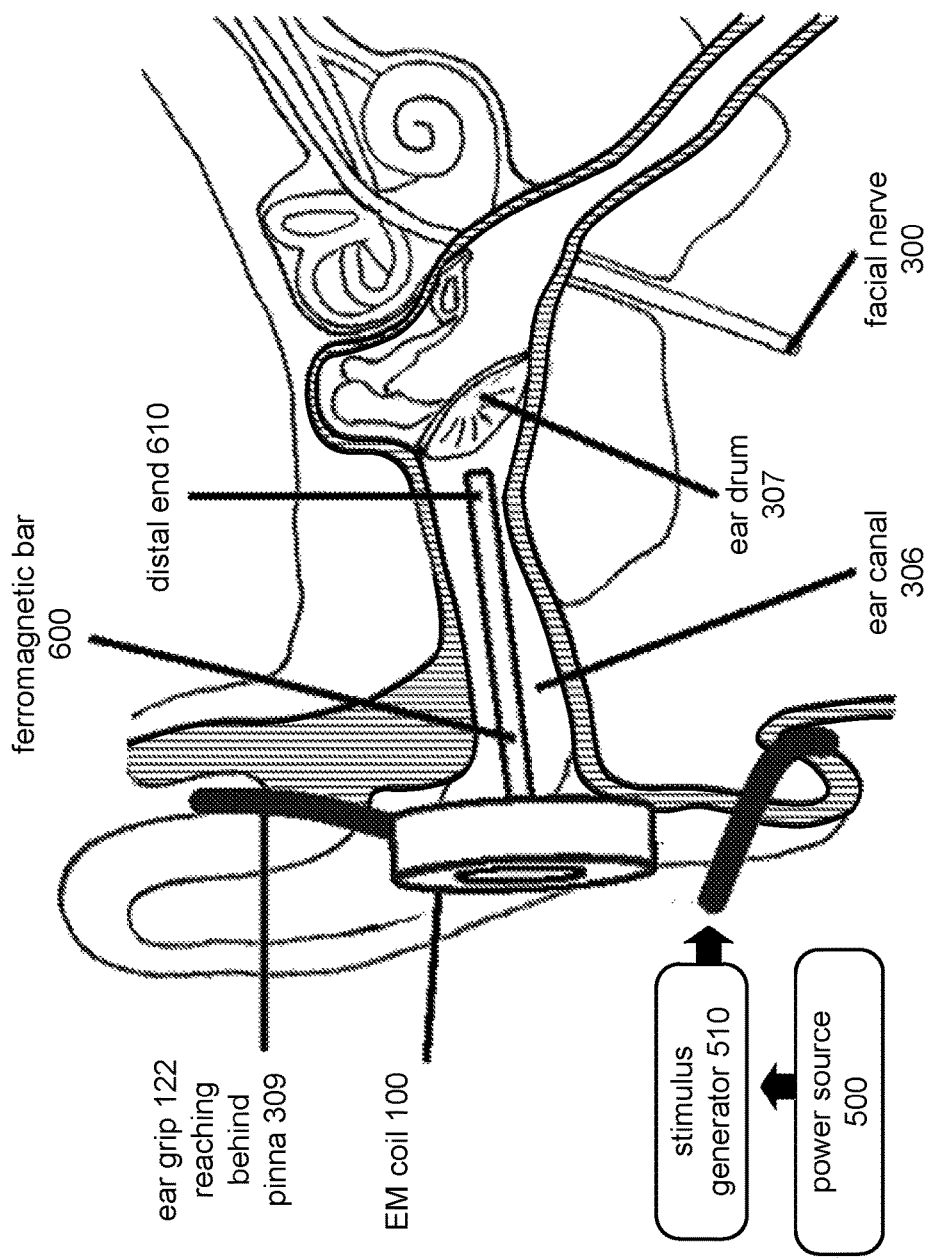
FIG. 10A depicts a single EM coil equipped with a laterally-placed ferromagnetic rod, in which the ferromagnetic rod extends into the ear canal.
Figure 10B:
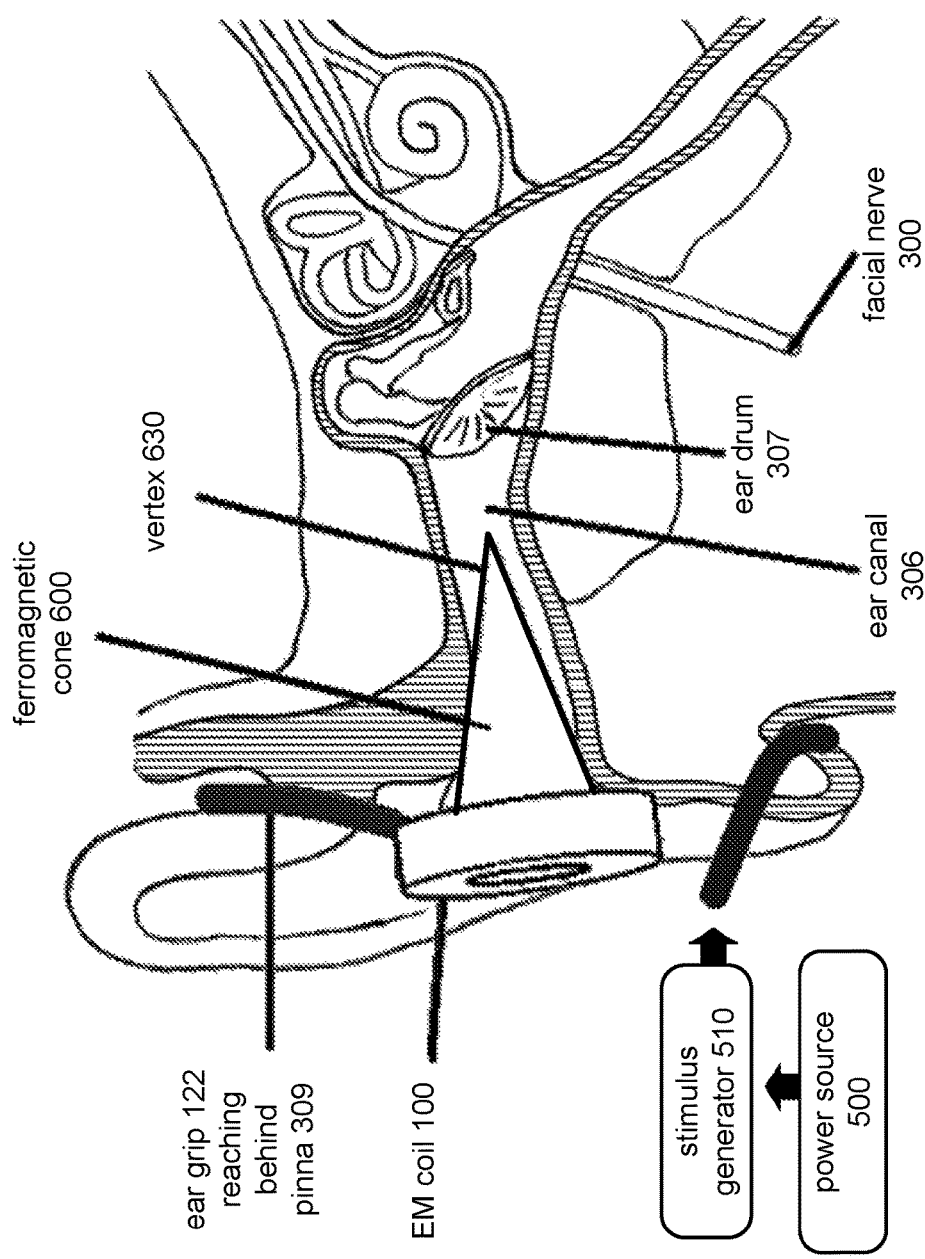
FIG. 10B depicts a single EM coil equipped with a ferromagnetic cone, in which the vertex of the ferromagnetic cone extends into the ear canal.

FIG. 10 depicts designs of the apparatus that involve a component composed of ferromagnetic metal or other EM-conducting material for the purpose of extending, shaping, directing, distorting, or otherwise changing the EM field generated by the EM coils 100. As shown in FIG. 10A, in some embodiments, a ferromagnetic bar 600 is placed on or attached to the face of an EM coil 100 such that magnetic energy is advanced through the ferromagnetic bar 600 to the distal end 610 of the ferromagnetic bar 600. The distal end 610 of the ferromagnetic bar 600 is placed in the ear canal near to the tympanic membrane/ear drum 307, thereby facilitating the delivery of the EM field 101 to the facial nerve 300 or a target part of the facial nerve system. In some embodiments, the ferromagnetic bar 600 has a 180-degree bend within the EM coil 100 so that the two ends of the ferromagnetic bar 600 are brought into proximity in an elongated "horseshoe" structure (not shown), and then the two ends of the ferromagnetic bar 600 are placed in proximity to the tympanic membrane/ear drum (not shown). In some embodiments, the ferromagnetic bar 600 has a 180-degree bend at its distal end 610 to create the elongated "horseshoe" structure, and then the bend of the ferromagnetic bar 600 is placed in proximity to the tympanic membrane/ear drum (not shown). In some embodiments, the proximal end of the ferromagnetic bar or other significantly linear ferromagnetic structure is placed in the central region of the EM coil 100, whereas in other embodiments it is placed on or around the body of the EM coil 100. In some embodiments, as shown in FIG. 10B, the ferromagnetic metal or other EM conducting material is shaped as a cone 620 with its base on the circumference or within the inner space of the EM coil 100, and its vertex 630 placed in the ear canal. In some embodiments, the ferromagnetic bar is composed of Permalloy or Mu-metal. In some embodiments, the EM field 100 carried by the ferromagnetic bar is focused or amplified by placement of ferromagnetic material in the facial nerve canal, fallopian aqueduct, or middle ear space. In some embodiments, the EM-conducting material is a gel that surrounds the EM coil(s) that protrudes or extends into the ear canal.

As shown in FIG. 11A-D, in some embodiments, a plurality of EM coils are employed in a manner to selectively stimulate part of the facial nerve system to the exclusion of other parts of the facial nerve system. In some embodiments, the EM coils generate EM fields that are directed at different parts of the facial nerve system. The coils can be angulated and separated in a constrained manner based on head size and shape so that the individual EM fields are reliably fixed on the different desired components of the facial nerve system. The EM fields generated by the multiple coils may be identical and synchronous or of different characteristics and/or asynchronous. In other embodiments, the EM coils may be arranged in a manner to eliminate, reduce, or counteract portions of the EM field that are not directed at the specific part of the facial nerve system targeted for stimulation.

Figure 11B:
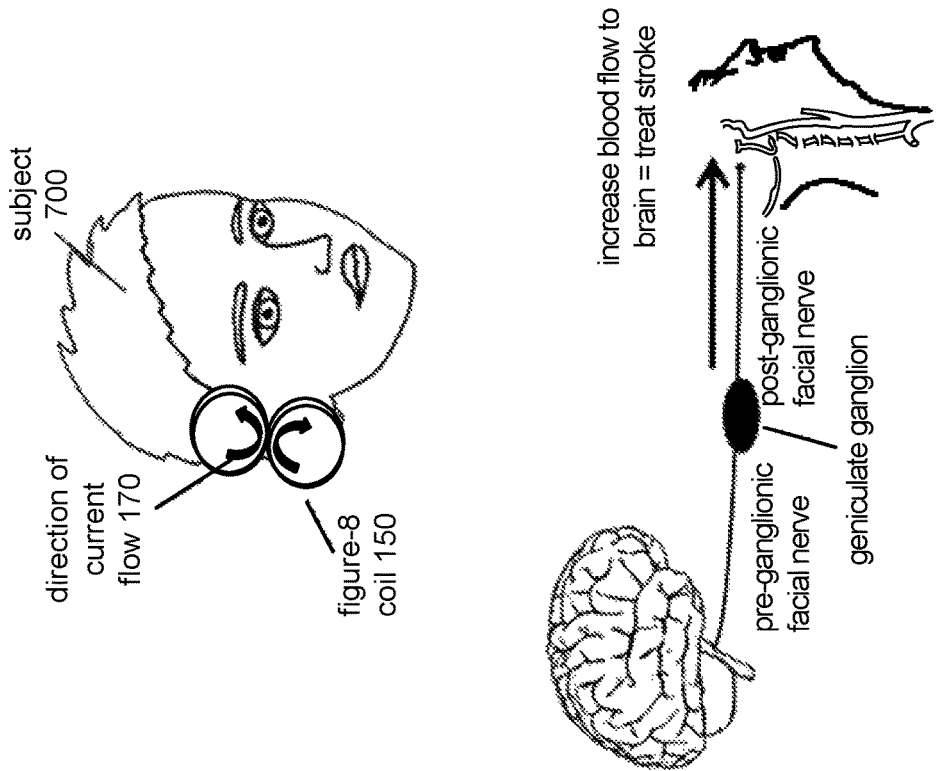
FIG. 11B depicts an assembly of four EM coils that exhibit convergence at their common central point equipped with a centrally-placed ferromagnetic rod.
Figure 11A:
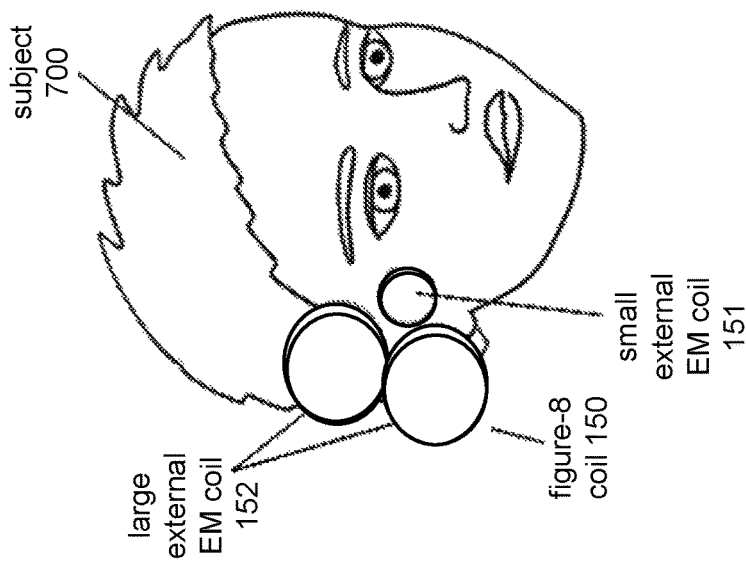
FIG. 11A depicts an assembly of three EM coils that are substantially round in design equipped with a centrally-placed ferromagnetic rod.

FIG. 11A shows an embodiment of the invention in which a plurality of EM coils generate EM fields that are directed at different parts of the facial nerve system. Here, multiple parts of the facial nerve system are stimulated for the purpose of inducing desired effects from one part of the facial nerve system while blocking undesired effects of another part of the facial nerve system. In this specific embodiment, a small external EM coil 151 is placed anterior to the ear, over the region of the parotid gland for the purpose of inhibiting action potentials carried by the external motor branches of the facial nerve, thereby reducing facial muscle movements. A pair of larger external EM coils 152 formed as a figure-8 coil 150 is then placed in a manner to direct its EM field at the geniculate ganglion or other part of the facial nerve system that is proximal to the brain from the post-ganglionic segment of the facial nerve system; stimulation from this component of the embodiment of the device acts to increase blood flow to the brain or cranium. In some embodiments, one or more EM coils receive alternating electrical current from the stimulus generator while other EM coils receive direct electrical current. In some embodiments, one or more EM coils generate pulses of magnetic field while other EM coils generate a constant magnetic field. In some embodiments, the apparatus also contains electrodes that can be applied to the subject for the purpose of delivering electrical current.

Figures 11C, 11D:
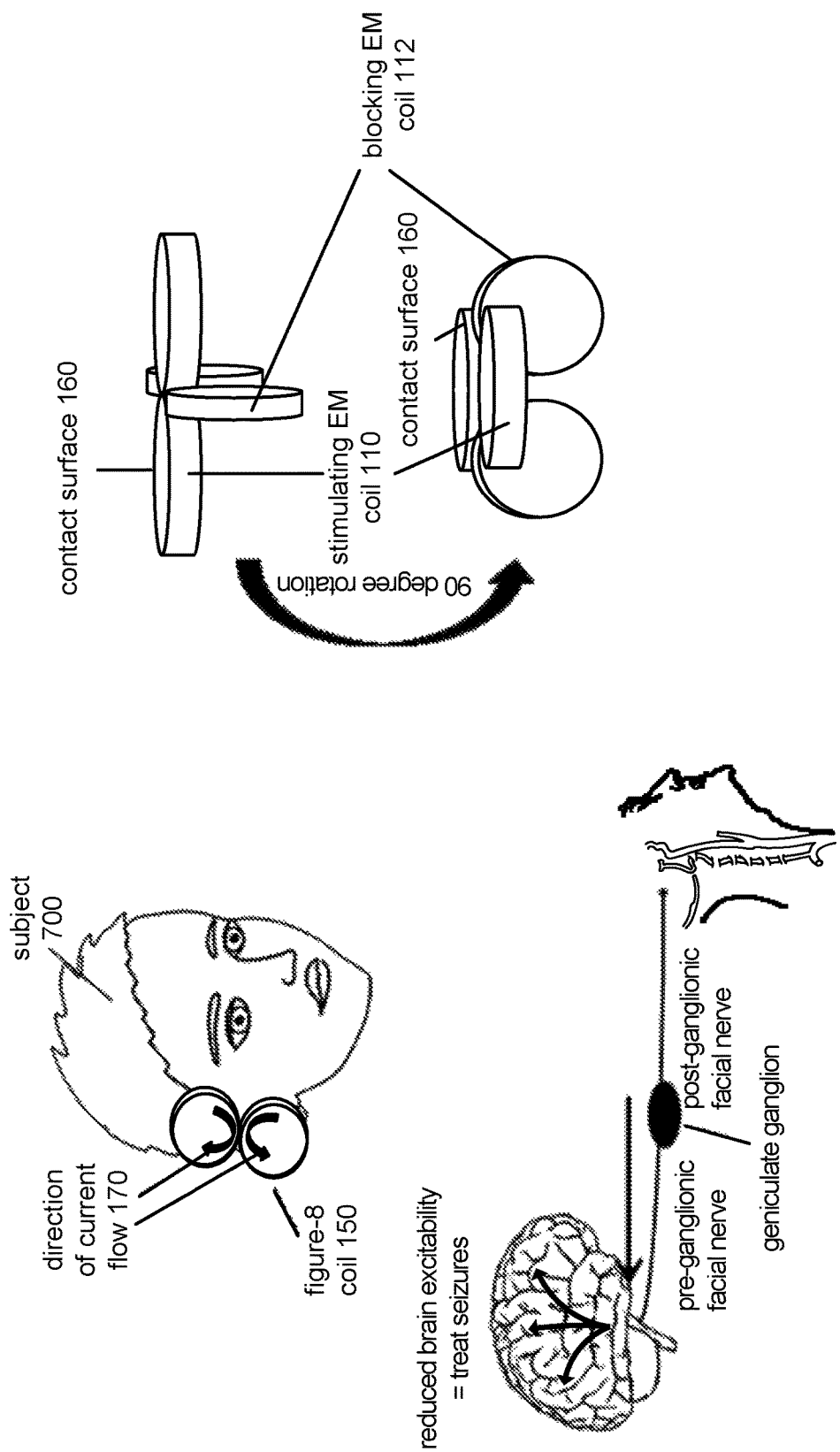
FIG. 11C depicts an assembly of four EM coils in which two of the EM coils are perpendicularly out-of-plane with the EM coils that are applied to the surface of a subject, for the purpose of blocking certain portions of the EM field.
FIG. 11D shows an embodiment of the deviced in which a plurality of EM coils are arranged such that two EM coils arranged as a figure-8 coil are used to activate the facial nerve system.

In some embodiments, the EM field or fields will be generated in a manner that directs action potential conduction in the facial nerve system to progress in a preferred direction, and/or that blocks propagation of the action potential in other directions, by selective direction of electrical current flow 170 through the EM coils. As shown in FIG. 11B, in some embodiments, action potentials are preferentially propagated away from the brain. An array of two EM coils arranged as a figure-8 coil 150 and placed over the right ear of the subject 700 conducts electrical current through the lower EM coil in a clockwise direction while conducting electrical current through the upper EM coil in a counter-clockwise direction. The EM field pulse is then generated in a manner that preferentially conducts action potentials from the target portion of the facial nerve system (here, the geniculate ganglion) away from the brain. In other embodiments of the invention, action potentials are preferentially propagated toward the brain. As shown in FIG. 11C, an array of two EM coils arranged as a figure-8 coil 150 and placed over the right ear of the subject 700 conducts electrical current through the lower EM coil in a counterclockwise direction while conducting electrical current through the upper EM coil in a clockwise direction. The EM field pulse is then generated in a manner that preferentially conducts action potentials from the target portion of the facial nerve system (here, the geniculate ganglion) toward the brain. In some embodiments of the invention, multiple parts of the facial nerve system are stimulated in such a manner for the purpose of colliding and neutralizing action potential propagation in certain parts of the facial nerve system. In some embodiments, a constant EM field is generated for the purpose of blocking local action potential conduction.

FIG. 11D shows an embodiment of the invention in which a plurality of EM coils are arranged such that two EM coils arranged as a figure-8 coil are used to activate the facial nerve system or portion thereof (stimulating EM coils 110) whereas another pair of EM coils arranged perpendicular to the figure-8 coil along its long axis and its bisecting axis are used to reduce, neutralize, or counteract unwanted portions of the EM field of the figure-8 coil (blocking EM coils 112). In some embodiments, the blocking EM coils 112 are removed or separated from the contact surface 160 of the stimulating EM coils 110.

Figure 12:
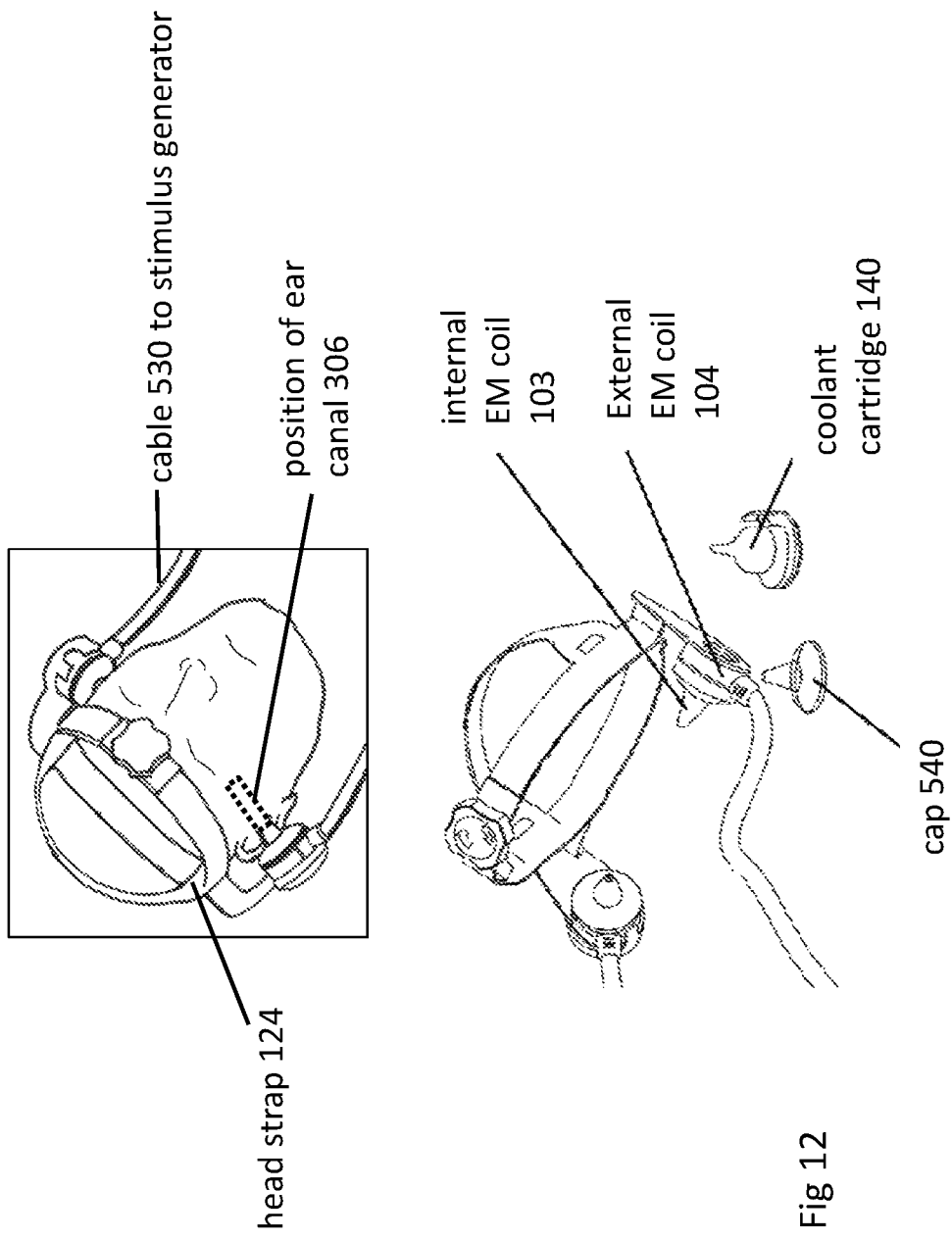
FIG. 12 depicts an apparatus for bilateral stimulation of the facial nerve in which a pair of EM coils is attached to each side of a head strap, and in which one of the EM coils of each pair is small enough to fit into the ear canal so that the apparatus is positioned in a manner to direct the EM fields at the desired part of the facial nerve system.

FIG. 12 depicts an apparatus for bilateral stimulation of the facial nerve system and/or target component of the facial nerve system. In this embodiment, a pair of EM coils is arranged on either side of the head near the ear and is supplied with stimulus energy from a stimulus generator by one or more cables 530. Each pair of EM coils is composed of (i) an external EM coil 104 shaped as a ring with a hollow center that is intended for placement against the side of the head over the external ear and (ii) an internal EM coil 103 that is sized and shaped so as to fit into the ear canal. In this example, the two EM coils of the pair of EM coils are contained in a single housing to maintain a precise spatial relationship with each other. A cap 540 composed of or containing a sound-dampening and/or heat-reflecting material or substance is placed over the internal EM coil 103 so as to provide the contact surface for the apparatus on the subject. In some embodiments, the cap 540 may be sterile.

Continuing with FIG. 12, the surface opposite the contact surface 160 of the apparatus may, in some embodiments, be designed to receive or connect to a coolant cartridge 140. In some embodiments, the coolant cartridge 140 may fill a central hole in the external EM coil 104 and provide a contact surface for the internal EM coil 103. A coolant cartridge 140 is then attached to the two EM coils that form a pair of EM coils with the following results: the external/non-subject side of the external EM coil 104 is covered by the coolant cartridge 140; the hollow center of the external EM coil 104 is filled by an extension of the coolant cartridge 140; the external/non-subject side of the internal EM coil 103 is in apposition to a projection of the coolant cartridge 140.

In other embodiments, the cap 540 is positioned on a head strap 124 in a manner that orients the generated EM field in a certain direction (not shown). In other embodiments, the cap is associated with positioning components or accessory devices that orient the generated EM field in a certain direction (not shown). In some embodiments, the cap 540 is composed of ferromagnetic material that distorts or modifies an electric or magnetic field in a desirable manner. In some embodiments, the cap 540, EM coils, or housing of the EM coils include one or more fiducial markers that indicate the expected direction or position of the EM field (not shown). In some embodiments, the cap 540 may incorporate aspects of a speculum for visualization of the tympanic membrane/ear drum.

In some embodiments, the coolant cartridge 140 connects to the EM coil in a manner that allows for electrical current to flow through the EM coil. In some embodiments, a connector or other component of the coolant cartridge 140 is irreversibly inactivated or destroyed by connection to the EM coil, thereby preventing reuse of the coolant cartridge 140. In some embodiments, electrical current flow through the EM coil serves to inactivate, destroy, or otherwise render as inoperable the connection between the coolant cartridge 140 and the EM coil.

Figure 13:
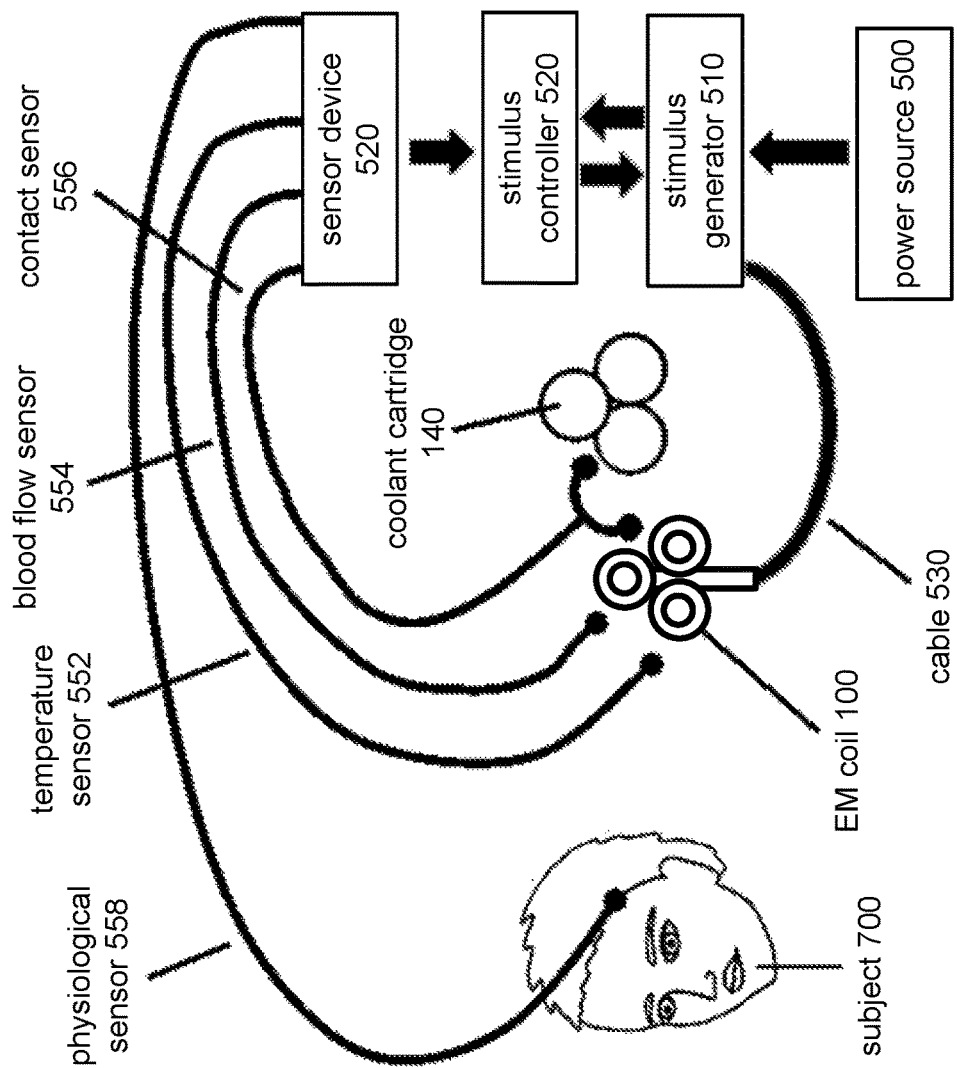
FIG. 13 depicts an apparatus for unilateral stimulation in which the stimulation controller is connected to several sensor devices placed on or between the stimulator, coolant cartridge, and subject.

As shown in FIG. 13, in some embodiments the EM coil 100 or assembly of more than one EM coil is supplied with electrical current through one or more cables 530 connecting to a stimulus generator 510. In some embodiments, the stimulus generator is supplied by or contains a power source 500 and is affected, directed, modulated, or instructed by a stimulus controller 520. In some embodiments, the stimulus generator 510 provides feedback to the stimulus controller 520 that affects the function of the stimulus controller 520.

In some embodiments, the stimulus controller 520 is affected, directed, modulated, or instructed by input or information it receives from one or more sensor devices 520. In some embodiments, a sensor device 520 is equipped with one or more sensors that can include physiological sensors 558, temperature sensors 552, blood flow sensors 554, contact sensors 556, and other sensors. In some embodiments, a sensor is directed at or placed on the EM coil 100, cable 530, coolant cartridge 140, or subject 700, or is directed at or placed between a combination of the EM coil 100, cable 530, coolant cartridge 140, and subject 700. Signal or information provided directly or indirectly to the stimulation controller 520 by sensors may, in some embodiments, change or instruct the function of the stimulus generator 510, EM coil 100, or a positioning component (as described for FIG. 1B), or else prompt an operator of the apparatus to modify the function of these parts of the apparatus.

Additional embodiments of the device may be adapted for use on different regions of the body. For example, an embodiment of the device may be adapted for stimulating the ganglia of the heart, lungs, major blood vessels, gut, or other organs. In such embodiments, the stimulation elements may be arranged as large coils placed on the ventral and/or dorsal aspects of the thorax or abdomen. As another example, an embodiment of the device may be adapted for stimulation of the cranial nerves coursing through the neck. In that embodiment, the stimulation elements may be arranged as a necklace with groupings of elements on one or both sides of the neck surface. In some embodiments, the group of elements focus stimulation energy at a target located deep to the anterior/carotid triangle of the neck. In other embodiments, the group of elements focus stimulation energy at a target located deep to the posterior/occipital triangle of the neck. In some embodiments, the target is the vagus nerve, the accessory nerve, the glossopharyngeal nerve, the hypoglossal nerve, a laryngeal nerve, the ansa cervicalis, a portion of the brachial plexus, or the ganglia of these neural structures. In other embodiments, the target is the carotid bulb or sinus.

Another embodiment of the device may be adapted for stimulation of the neural structures near to, or derived from, the spine. In some embodiments, stimulation elements are arranged as chains longitudinally placed alongside the spine on the posterior surface of the neck or on the back. In some embodiments, the target for stimulation includes the phrenic nerve, the spinal sympathetic chain, an occipital nerve, a portion of the brachial plexus, or the ganglia of these neural structures.

In some embodiments, different regions of the body are stimulated in conjunction with stimulation of the facial nerve.

Neural Structure Modulation Methods

Referring now to FIG. 14, there is shown a flow diagram providing a method for neural structure modulation, according to an embodiment of the invention. It should be understood that these steps are illustrative only. Different methods of the invention may perform the illustrated steps in different orders, omit certain steps, and/or perform additional steps not shown in FIG. 14 (the same is true for the other Figures). The method can start and end at various points in the process, and often the method is a continuous process with multiple steps occurring simultaneously, so the Figures provide only examples of one ordering of method steps. In addition, the method can be performed using any of the apparatuses described herein or other apparatuses capable of performing the steps provided below.

As shown in FIG. 14, the method includes an initial step for application of the apparatus to the body, such as for placement 1000 of the apparatus on the head. In some embodiments, placement 1000 of apparatus on the head involves the unilateral application of an apparatus. In other embodiments, placement 1000 of apparatus on head involves application of an apparatus to both sides of the head or application of one apparatus to each side of the head. In some embodiments, for safety purposes, the apparatus can detect 1004 whether a condition exists that would interfere with stimulation of the neural system of the subject with the apparatus. For example, the apparatus can detect 1004 whether a material, such as a metal, is on or inside of the subject near to the stimulation components of the apparatus before use. Presence of a metal might provide an unsafe condition since the apparatus will be generating an EM field. Thus, the detection 1004 can notify the user that the metal is present such that the metal can be removed before an EM field is generated. In these embodiments, once the apparatus is applied to the head and is in a suitable position for use, the apparatus is employed in a manner that allows the apparatus (e.g., the electrically-conductive element(s), such as the EM coils) to detect 1004 the local presence of metal. In another embodiment, the detection is a question-and-answer review with, and observation and examination of, a subject performed by the user of the apparatus.

In response to the detection of the conditions (such as detection of a metal), the apparatus can perform an adjustment to remove or alleviate this condition. In one embodiment, the detection of metal will cause the method to end 1200 and the apparatus may shut down or be unwilling to operate until the metal is no longer detected. In other embodiments of the method, the apparatus will cause an alarm to sound that informs an operator of the local presence of metal on the subject. In this method, failure to detect 1004 the local presence of metal can be required, but is not necessarily sufficient, for activation of the apparatus (i.e., activation can require other steps in some embodiments, such as attachment of coolant cartridges to the EM coils 1008). In another embodiment, the adjustment performed is removal of the metal by a user or informing of the subject that the metal must be removed or that the procedure cannot be performed. In a further embodiment, the condition detected is that the apparatus requires cooling, and the apparatus absorbs or dissipates heat. For example, the apparatus may have a cooling cartridge to absorb or dissipate heat, or the user may attach such a cooling cartridge. In another embodiment, the method includes providing a functional nerve block for application, such as to a pure somatic motor or a somatic sensory component of the neural system, thereby improving tolerability of the simulation by the subject. This can be provided to the subject by the apparatus or by a user of the apparatus. For example, the apparatus can deliver a pharmacologic agent, or the user can provide the agent (e.g., topically or as an injection). Additionally, the nerve block may be an electrical current applied by an electrode of the stimulator apparatus or the nerve block is an electromagnetic field created by one of a plurality of electrically-conductive wire arrays of the stimulator apparatus.

With this detection 1004 step achieved, the stimulus controller can be programmed (if necessary) and activated 1014 in embodiments that include such a stimulus controller. In these embodiments, the stimulus controller directs or allows the activation 1018 of the stimulus generator, which then delivers stimulus energy (e.g., electrical current) to the electrically-conductive element (e.g., an EM coil). Thus, stimulation energy can be administered to the subject by the apparatus (e.g., controlled by the operator of the apparatus) for a period of time to generate an electromagnetic field to stimulate the neural system of the subject. In one embodiment, electrical current is delivered 1020 to a first set of EM coils and delivered 1024 to a second set of EM coils. In some embodiments, the first set of EM coils is composed of EM coils placed on one side of the head and the second set of EM coils is composed of EM coils placed on the other side of the head. In some embodiments, the first set of EM coils are EM coils placed in the ear canal and the second set of EM coils are external EM coils placed on the side of the head. In some embodiments, the delivery 1020 of electrical current to the first set of EM coils is initiated before the delivery 1024 of electrical current to the second set of EM coils. In other embodiments, the delivery 1020 of electrical current to the first set of EM coils is of a different voltage, current, duration, and/or waveform than is the delivery 1024 of electrical current to the second set of EM coils and the electrical current is delivered to the two sets of EM coils simultaneously.

The stimulation energy can be delivered 1024 as electromagnetic pulses. In one example, these pulses are of biphasic shape and of 100-450 microseconds in duration and 0.5-2.0 Tesla field strength at a surface of the apparatus. In another example, the electromagnetic pulses are delivered at 5-20 Hertz frequency in a continuous manner for less than 5 minutes. The stimulation can also be delivered intermittently. In one example, the duration, intensity, frequency, waveform, or other parameter of the administered stimulation energy as a function of blood flow, electroencephalography potentials, intracranial pressure, a duration of the condition of the subject, or other physiological or pathophysiological parameter.

Continuing with FIG. 14, following delivery of the stimulus energy to the electrically-conductive element(s) (e.g., delivery 1020, 1024 of electrical current to the EM coils), the need for further stimulation is determined by a component of the apparatus, such as the stimulus generator. The apparatus thus assesses whether continued stimulation is needed to treat the subject after the period of stimulation time has elapsed. In some embodiments, a minimum stimulation time must be achieved 1028 before termination of the stimulation. If the minimum stimulation time is not achieved, the stimulus generator is activated 1018 and the delivery 1020, 1024 of electrical current to the EM coils repeats. If the minimum stimulation time is achieved or it is otherwise determined that continued stimulation is not needed, the stimulation process ends 1200 and stimulation is discontinued. As another example, the determination of whether continued stimulation is needed is based on delivery of a certain number of stimulus pulses. In a further example, the determination is based upon feedback from the subject or feedback from a sensor associated with the apparatus The method also includes providing power via a power source for supplying the stimulus energy to the electrically-conductive elements, such as the EM coils (the power may also be provided automatically, as the device may be constantly connected to or in communication with the power source). The power can be provided via wires connecting the power source to the device. In some methods, supplying stimulus energy to the EM coil or coils modulates blood flow to the brain of the subject or enhances delivery of a blood-borne pharmacologic agent to treat stroke or another condition of the subject. In some methods, supplying stimulus energy to the EM coil or coils modulates electroencephalographic activity (e.g., of the cerebral cortex) to treat or prevent seizures or another condition of neural excitability/inactivity of the subject. The modulation can be performed in the condition or expectation of epilepsy and seizure disorders as either the direct treatment of a disease process or else to prevent onset of the disease process.

If any adjustments are needed or desired regarding the stimulus energy, the method can include adjusting the stimulus energy. For example, the adjustments can be made based on physiological or pathophysiological responses of the subject to the stimulus energy. The method can continue with supplying and adjusting as needed until the method is done. When the method is done (i.e., the treatment is successful and complete), the apparatus can be removed from the subject. If the apparatus has a detachable cap, the method can include detaching the cap and attaching a new cap. If the apparatus has a detachable coolant cartridge, the method can include detaching the coolant cartridge and attaching a new coolant cartridge.

Referring now to FIG. 15, there is shown a method of facial nerve system stimulation, according to an embodiment of the invention, in which sensor feedback regulates the use of the apparatus. In this embodiment, placement 1100 of the apparatus on the body (e.g., on the head) is followed by attachment or application of a blood flow sensor to the subject. Then a baseline blood flow measurement is obtained 1132 and a threshold defining blood flow increase is set 1134. In some embodiments, other or additional sensors can also be applied to regulate use of the apparatus. In some embodiments, these sensors may detect properties of the apparatus or of the subject including but not limited to the following: carotid artery blood flow; cerebral artery blood flow; blood flow to the central nervous system; facial nerve electrical potentials; skin/scalp galvanic responses; skin/scalp blood flow; ear temperature; pupilometry; intraocular pressure; blood flow to the eye; bioelectric potentials; electroencephalogram waveforms; electrophysiological testing of the auditory or vestibular systems; taste sensation; audition; lacrimation; nasal drainage; nasal congestion; salivation; sound sensitivity; face, head, or hand movements or electromyographic potentials; speech production or arrest; sensation of body movement; eye movements; cranial blood flow; direct or indirect activity of a nerve; and severity of neurological dysfunction of the subject. In some embodiments 1114, the stimulus controller is entirely pre-programmed and cannot be adjusted or programmed by a user of the apparatus (although in other embodiments it can be programmable). In some embodiments, the stimulus controller offers a minimum of stimulation options that can be selected by a user. In some embodiments, the stimulation options offered by the stimulus controller 1114 are adjusted, altered, restricted, or enhanced by feedback, information, or signals provided to the stimulus controller 1114 by sensors and/or sensor devices to the apparatus.

Continuing with FIG. 15, the stimulus generator is activated 1118 and delivers electrical current to the electrically-conductive element(s) (e.g., delivers 1120 electrical current to a first set of EM coils). In some embodiments, as a subsequent or simultaneous step, the stimulus generator delivers energy, such as electrical current, to an electrically conductive element such as a second set of EM coils 1124. Steps 1120 and 1124 in this method may be sequential or simultaneous, and/or may be distinct in terms of the quantity, polarity, duration, waveform, or other parameter of the electrical current. In some embodiments, the first set of EM coils is composed of EM coils placed on one side of the head and the second set of EM coils is composed of EM coils placed on the other side of the head. In some embodiments, the first set of EM coils are EM coils placed in the ear canal and the second set of EM coils are external EM coils placed on the side of the head. In some embodiments, the first set of EM coils may be placed in the vicinity of the ears and the second set may be placed elsewhere on the head (e.g., inside the mouth or under the chin).

Upon delivery 1120, 1124 of electrical current to the EM coils, the stimulus controller then determines if a minimum stimulation time has not been achieved 1130 for blood flow assessment, and if the minimum stimulation time has not been achieved then the steps described in 1118, 1120, 1124 are repeated. Once the stimulus controller determines that a sufficient duration since the time of activation has been achieved to perform a blood flow measurement, it inactivates the stimulus energy delivery 1132 and activates 1134 the blood flow sensor. The purpose of this step is to determine if the stimulation of the facial nerve system or portion of the facial nerve system has achieved the desired result, namely, to achieve 1140 a threshold for increase of blood flow.

In some embodiments, measurement of blood flow is achieved by use of two or more EM coils, one or more of which serve to magnetize nearby blood while the others serve to detect the release or decay of energy from the magnetized blood once it has moved in a cranial or rostral direction, as described in FIG. 5. Returning to FIG. 15, in some embodiments, means of measuring blood flow in the head, neck, brain, or other anatomical structure 1130 other than magnetization of blood are employed for determining of blood flow measurement to achieve threshold for increase 1140. If the threshold for blood flow increase is achieved 1140, the process ends 1210. If the threshold for blood flow increase is not achieved 1140, the stimulus generator is activated 1118 for delivery of stimulus energy and additional electrical current is delivered 1120, 1124 to the EM coils, and the process repeats.

The method can also include monitoring one or more physiological or pathophysiological responses of the subject over a period of time. In this method, if it is determined that an adjustment is needed, the method can include adjusting the intensity, frequency, pattern, etc. of the stimulus energy supplied to the EM coils. The adjustment can be made based on the one or more physiological or pathophysiological responses of the subject, the decision of a user, or based on other factors. In some methods, the adjustment can occur automatically without requiring any action by a physician, operator, or other user to make the adjustment. In other methods, the physician, operator, or other user can have access to the monitored responses of the subject, and can control the adjustment based on the monitoring. The method can include continued supplying of stimulus energy to the EM coils with periodic monitoring and adjusting as needed over a period of time to treat the subject, or monitoring can be continuous until a sensor signal is received or a threshold is crossed that causes reactivation of the apparatus leading to the delivery of additional stimulation energy. In this manner, if stimulation is needed or desired of one or more components of the facial nerve system to dilate vessels and treat stroke and/or prevent stroke recurrence, the device can provide such stimulation. This can be done automatically or under the control of a physician, operator, or other user using the device.

In some methods of use, repeating stimulation between intervals of non-stimulation is desirable and expected. In some methods of use, the interval between periods of stimulation is defined by the blood flow response. In other methods of use, the interval between periods of stimulation is predetermined. In some methods of use, the stimulation parameters employed in second and subsequent stimulations is differently set than the initial stimulation parameters. In some embodiments, the stimulation parameters used in the initial or subsequent stimulations are set so as to induce long-term or other types of neural potentiation. In some embodiments, long-term or other types of neural potentiation involve the geniculate ganglion, sphenopalatine ganglion, brainstem, or other neuron groups.

In some methods-of-use, the sensor device detects and/or interprets electroencephalographic potentials, and informs the activity of the stimulus controller based on that information.

In some methods-of-use, the sensor device measures and/or interprets intracranial pressure, and informs the activity of the stimulus controller based on that information.

In some methods-of-use, failure of the apparatus to achieve the desired result will be followed by filling the ear canal with electrically-conductive materials, gels, or solutions, and/or anesthetics and/or pharmacological substances. Once filling of the ear canal is complete, stimulation of the facial nerve system with the apparatus may be attempted again. In some embodiments, the electrically-conductive material, gel, solution, or anesthetics and/or pharmacological substances placed into the ear canal surrounds or otherwise encompasses the EM coils of the apparatus.

In some methods-of-use, failure of the apparatus to achieve the desired result will be followed by advancement of a cannula into the middle ear space. In this situation, a hole is punctured in the ear drum using a sharpened distal end of a cannula. The cannula is equipped so as to allow injection of electrically-conductive materials, gels, solutions, or anesthetics and/or pharmacological substances. Once injection into the middle ear space is complete, stimulation of the facial nerve system with the apparatus may be attempted again. Puncture of the ear drum in order to obtain access to the middle ear space may be facilitated by a stereotaxic device that positions the distal end of the cannula, or by fiber optic visualization. Alternatively, puncture of the ear drum may be accomplished by means of a pressure-sensitive distal end of the cannula or by electrical conductivity changes at the distal end of the cannula.

In some methods-of-use, conduction block of extracranial/distal facial nerve is applied prior to, or during, stimulation of the facial nerve system. In some methods-of-use, the conduction block is accomplished by a local injection of a pharmacological substance into the face or head. In some methods-of-use, the conduction block is accomplished by application of an electrical current across or in the vicinity of the facial nerve trunk external to the middle ear. In some methods-of-use, the conduction block is accomplished by generation of a constant EM field in the vicinity of the facial nerve trunk external to the middle ear.

In some methods-of-use, stimulation of the facial nerve system with EM fields in frequencies of 5-20 Hertz may be optimal for inducing the desired effect. In some methods-of-use, stimulation patterns involving on-off periods may be optimal for inducing the desired effect. In some methods-of-use, stimulation strengths of 0.5-2.0 Tesla (8-32 kT/s at coil surface) may be optimal for inducing the desired effect. In some methods-of-use, stimulation waveform width of 100-450 microseconds may be optimal for inducing the desired effect. In some methods-of-use, stimulation waveform shapes that are substantially bipolar may be optimal for inducing the desired effect. In some methods-of-use, stimulation may be maintained for 0.5 to 5 minutes in duration. In some methods-of-use, the stimulation parameters, direction of electrical current, the orientation of the EM coils, and/or the configuration of the EM coils may be changed depending upon the condition of the patient.

In some methods, use of the apparatus may be appropriate in disorders of cerebrovascular circulation (stroke, chronic cerebrovascular atherosclerosis), head trauma, dementia, headache disorders, or other neurological conditions. In some methods, use of the stimulator may be appropriate prior to procedures that involve the cerebral and carotid arteries, such as endovascular clot retrieval during stroke, endovascular coil and stent placement in aneurysmal subarachnoid hemorrhage, diagnostic angiography, or surgical carotid endarterectomy. In some methods, use of the device may interrupt seizure activity, reduce the likelihood of developing a seizure, or prevent the development of epilepsy. In some methods, use of the apparatus may modulate intracranial pressure. In some embodiments, use of the stimulator may modulate inflammatory and immune reactions within or of the head, neck, and/or elsewhere in the body.

While the present teachings are described in conjunction with various embodiments and methods, it is not intended that the present teachings be limited to such embodiments. On the contrary, the present teachings encompass various alternatives, modifications, and equivalents, as will be appreciated by those of skill in the art. Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

What is claimed is:

1. A method of stimulating a portion of a neural system of a subject through an ear of the subject, via a stimulator apparatus having a stimulus generator, one or more electrically-conductive elements, and an energy regulating housing adapted to contain and to electrically insulate the one or more electrically-conductive elements and to dissipate heat, the method comprising:
    delivering, via the stimulus generator, stimulus energy to the one or more electrically-conductive elements for a specified period of time to stimulate the portion of the neural system of the subject through an ear of the subject;
    after lapse of the specified period of time, assessing whether criteria for ceasing stimulation are satisfied, the criteria comprising a threshold for blood flow increase that is set based on a baseline blood flow measurement; and
    based on the assessing:
        responsive to determining that the criteria for ceasing stimulation are satisfied, ceasing delivery of the stimulus energy via the stimulus generator, or
        responsive to determining that the criteria for ceasing stimulation are not satisfied, adjusting delivery of the stimulation energy until the criteria are satisfied.

2. The method of claim 1, wherein delivering the stimulus energy comprises:
    enabling positioning of the stimulator apparatus in a vicinity of the portion of the neural system of the subject by:
        arranging a first surface of the energy regulating housing to face the subject and rest against an external ear of the subject, the first surface comprising materials having lower thermal conductivity than other surfaces of the housing;

inserting a positioning ear piece into an ear canal of the subject, the positioning ear piece enclosed by a second surface comprising heat resistant materials; and arranging a third surface of the energy regulating housing to face away from the subject, the third surface comprising materials having a higher thermal conductivity than the first surface, wherein the first, second, and third surfaces are electrically insulating.

3. The method of claim 1, further comprising:

determining whether a condition exists that would interfere with stimulation of the portion of the neural system of the subject with the stimulator apparatus; and responsive to determining existence of an interfering condition, performing an adjustment to remove or alleviate the interfering condition.

4. The method of claim 3, wherein determining existence of the interfering condition comprises detecting, via the one or more electrically conductive elements, presence of an object comprising a metallic material within a specified vicinity of the stimulator apparatus.

5. The method of claim 3, wherein performing the adjustment further comprises absorbing or dissipating heat from the apparatus.

6. The method of claim 1, further comprising providing a functional nerve block for application to a pure somatic motor or a somatic sensory component of the neural system of the subject to improve tolerability of the simulation by the subject.

7. The method of claim 6, wherein the nerve block is a pharmacological agent.

8. The method of claim 6, wherein the nerve block is an electrical current applied by an electrode of the stimulator apparatus.

9. The method of claim 6, wherein the nerve block is an electromagnetic field created by at least one of the one or more electrically-conductive elements of the stimulator apparatus.

10. The method of claim 1, wherein delivering the stimulus energy further comprises delivering, by the stimulus generator, electromagnetic pulses.

11. The method of claim 10, wherein the electromagnetic pulses are of substantially biphasic shape and are of 100-450 microseconds duration and 0.5-2.0 Tesla-field strength.

12. The method of claim 10, wherein the electromagnetic pulses are delivered at 5-20 Hertz frequency in a continuous manner for less than 5 minutes.

13. The method of claim 1, wherein the stimulus energy is delivered intermittently.

14. The method of claim 1, wherein assessing whether criteria for ceasing stimulation are satisfied comprises determining whether a specified amount of time has lapsed from an onset of the stimulation or determining whether a specified number of stimulus pulses have been delivered.

15. The method of claim 1, wherein assessing whether the criteria for ceasing stimulation are satisfied further comprises evaluating feedback obtained from the subject or a feedback signal measured from a sensor associated with the apparatus to determine whether the criteria for ceasing stimulation are satisfied.

16. The method of claim 1, wherein assessing whether the criteria for ceasing stimulation are satisfied comprises measuring a parameter of the delivered stimulus energy and comparing the measured parameter against a specified threshold value.

17. The method of claim 1, further comprising obtaining the baseline blood flow measurement with a sensor of the apparatus; and setting the threshold for blood flow increase based on the baseline blood flow measurement.

18. The method of claim 1, wherein delivering the stimulus energy further comprises setting a duration, intensity, frequency, or waveform, as a function of blood flow, electroencephalography potentials, intracranial pressure, or a duration of a condition of the subject.

19. The method of claim 1, further comprising:

determining efficacy of the delivery of stimulus energy; and responsive to determining that the efficacy was insufficient, enabling insertion of an electrically-conductive material, pharmacological agent, or anesthetic in a portion of an ear of the subject.

* * * * *

UNITED STATES PATENT AND TRADEMARK OFFICE
CERTIFICATE OF CORRECTION

PATENT NO. : 10,105,549 B2
APPLICATION NO. : 15/056326
DATED : October 23, 2018
INVENTOR(S) : Mark Klingler Borsody Page 1 of 1

It is certified that error appears in the above-identified patent and that said Letters Patent is hereby corrected as shown below:

On the Title Page

Item (57), Abstract, Lines 11 & 12: "chronically variations for long-term maintenance" to read as —chronic variations for long-term maintenance—

Signed and Sealed this
Twenty-fourth Day of December, 2019

Andrei Iancu
*Director of the United States Patent and Trademark Office*